(12) United States Patent
Tsien et al.

(10) Patent No.: US 7,332,598 B2
(45) Date of Patent: *Feb. 19, 2008

(54) NON-OLIGOMERIZING TANDEM FLUORESCENT PROTEINS

(75) Inventors: Roger Y. Tsien, La Jolla, CA (US); Robert E. Campbell, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 404 days.

This patent is subject to a terminal disclaimer.

(21) Appl. No.: 10/885,988

(22) Filed: Jul. 6, 2004

(65) Prior Publication Data

US 2004/0259165 A1    Dec. 23, 2004

Related U.S. Application Data

(63) Continuation of application No. 09/866,538, filed on May 24, 2001, now Pat. No. 6,852,849, which is a continuation-in-part of application No. 09/794,308, filed on Feb. 26, 2001, now Pat. No. 7,022,826.

(51) Int. Cl.
- *C07H 21/04* (2006.01)
- *C07K 14/00* (2006.01)
- *C12N 15/09* (2006.01)

(52) U.S. Cl. ............... 536/23.7; 435/69.1; 435/320.1; 435/325; 530/350

(58) Field of Classification Search ............... 536/23.7; 435/69.1, 320.1, 325; 530/350
See application file for complete search history.

(56) References Cited

U.S. PATENT DOCUMENTS

| 5,625,048 A | 4/1997 | Tsien et al. | |
|---|---|---|---|
| 6,852,849 B2 * | 2/2005 | Tsien et al. | 536/23.7 |
| 7,022,826 B2 * | 4/2006 | Tsien et al. | 536/23.1 |

FOREIGN PATENT DOCUMENTS

| WO | WO 96/23810 | 8/1996 |
|---|---|---|
| WO | WO 00/34318 A | 6/2000 |
| WO | WO 00/34326 | 6/2000 |
| WO | WO 00/34526 | 6/2000 |
| WO | WO 01/62919 | 8/2001 |
| WO | WO 01/96373 | 12/2001 |

OTHER PUBLICATIONS

Ormö, Mats, et al., "Crystal Structure of the *Aequorea victoria* Green Fluorescent Protein", Science, vol. 273, pp. 1392-1395, Sep. 6, 1996.
Yanushevich, Yurii G., et al., "A Strategy for the Generation of Non-Aggregating Mutants of *Anthozoa* Fluorescent Proteins", FEBS Letters 511, pp. 11-14, 2002.
Baird, et al., "Circular Permutation and Receptor Insertion Within Green Fluorescent Proteins", *Proc. Natl. Acad. Sci. USA*—96:11241-11246 (1999).
Baird, et al., "Biochemistry Mutagenesis and Oligomerization of DsRed, a Red Fluorescent Protein From Coral", *Proceedings of the National Academy of Sciences of the United States of America*—97(22):11984-11989 (2000).
BD Biosciences/Clontech, Product Literature, "Living Colors DsRed C-Terminal Fusion Vector", *CLONTECHniques*, p. 22, (Jan. 2000).
BD Biosciences/Clontech, Product Literature, "Living Colors Red Fluorescent Protein", *CLONTECHniques*—vol. XIV, No. 4, pp. 2-6 (Oct. 1999).
BD Biosciences/Clontech, Product Literature, "Mercury DsRed1 Signaling Probes" *CLONTECHniques*, pp. 22 & 23 (Apr. 2000).
Campbell et al., "A Monomeric Red Fluorescent Protein" *PNAS*—99(12):7877-7882 (2002).
Gross, et al., "the Structure of the Chromophore Within the DsRed, a Red Fluorescent Protein From Coral", *Proceedings of the National Academy of Sciences of the United States of America*—97(22):11990-11995 (2000).
Heim, et al., "Improved Green Fluorescence", *Nature*—373:663-664 (1995).
Heim, et al., "Wavelength Mutations and Posttranslational Autoxidation of Green Fluorescent Protein", *Proc. Natl. Acad. Sci. USA*—91:12501-12504 (1994).
Lauf, et al., "Expression of Fluorescently Tagged Connexins: A Novel Approach to Rescue Function of Oligomeric DsRed-Tagged Proteins", *FEBS Lett*—498:11-15 (2001).
Lukyanov, et al., "Natural Animal Coloration Can be Determined by a Nonfluorescent Green Fluorescent Protein Homolog", *J. Biol. Chem.*—275:25879-25882 (2000).

(Continued)

*Primary Examiner*—Chih-Min Kam
(74) *Attorney, Agent, or Firm*—Townsend and Townsend and Crew LLP

(57) ABSTRACT

Non-oligomerizing fluorescent proteins, which are formed by operatively linking two or more monomers of a fluorescent protein, or which are derived from a fluorescent protein having at least one mutation that reduces or eliminates the ability of the fluorescent protein to oligomerize, are provided. The non-oligomerizing fluorescent proteins can be derived from a naturally occurring green fluorescent protein, a red fluorescent protein, or other fluorescent protein, or a fluorescent protein related thereto. Also provided is a fusion protein, which includes a non-oligomerizing fluorescent protein linked to at least one polypeptide of interest. In addition, a polynucleotide encoding a non-oligomerizing fluorescent protein is provided, as is a recombinant nucleic acid molecule, which includes polynucleotide encoding a non-oligomerizing fluorescent protein operatively linked to at least a second polynucleotide. Vectors and host cells containing such polynucleotides also are provided, as are kits containing one or more non-oligomerizing fluorescent proteins or encoding polynucleotides or constructs derived therefrom. Further provided are methods of making and using the proteins and polynucleotides.

20 Claims, 1 Drawing Sheet

OTHER PUBLICATIONS

Matz, et al., "Fluorescent Proteins From Nonbioluminescent Anthozoa Species", *Nature Biotechnology*—17:969-973 (1999).

Miyawaki and Tsien, "Monitoring Protein Conformations and Interactions by Fluorescence Resonance Energy Transfer Between Mutants of Green Fluorescent Protein", *Methods Enzymol. Application of Chimeras in Cell Physiology*—327:472-500 (2000).

Miyawaki, et al., "Dynamic and Quantitative CA2+ Measurements Using Improved Cameleons", *Proc. Natl. Acad. Sci. USA* 13 96:2135-2140 (1999).

Prasher, et al., "Summary Structure of the Aequorea Victoria Green-Fluorescent Protein", *Gene*—111:229-233 (1992).

Roth, et al., "Purification & Protease Susceptibility of the Green-Fluorescent Protein of Aequorea With a Note on Hlistaura", *Thesis from the Graduate Program in Biochemistry from Rutgers, the State University of New Jersey* (1985).

Tsien, R., "Rosy Dawn for Fluorescent Proteins" *Nature Biotechnology*—17:956-957 (1999) and Nucleotide search results, Accession No. AF168419.

Wall, et al., "The Structural Basis for Red Fluorescence in the Tetrameric GFP Homolog DsRed", *Nature Struct. Biol.*, —7:1133-1138 (2000).

Wiehler, et al., "Mutants of Discosoma Red Fluorescent Protein With a GFP-Like Chromophore" *FEBS Letters*—487:384-389 (2001).

Yang, et al., "the Molecular Structure of Green Fluorescent Protein", *Nature Biotechnology*—14(10):1246-1251 (1996).

Yarbrough, et al., "Refined Crystal Structure of DsRed, a Red Fluorescent Protein From Coral, at 2.0-A Resolution", *Proc. Natl. Acad. Sci. USA*—98:462-467 (2001).

* cited by examiner

NON-OLIGOMERIZING TANDEM FLUORESCENT PROTEINS

This application is a continuation of U.S. patent application Ser. No. 09/866,538, filed May 24, 2001, now U.S. Pat. No. 6,852,849, which is a continuation-in-part application of U.S. patent application Ser. No. 09/794,308, filed Feb. 26, 2001, now U.S. Pat. No. 7,022,826, the entire contents of both of which is applications are incorporated herein by reference and from both of which applications priority is claimed under 35 U.S.C. § 120.

This invention was made in part with government support under Grant No. NS 27177 by the National Institute of Neurological Disorders and Stroke and Grant No. GM 62114-01 awarded by the National Institute of General Medical Sciences. The government has certain rights in this invention.

BACKGROUND OF THE INVENTION

1. Field of the Invention

The present invention relates generally to fluorescent proteins, and more specifically to tandem fluorescent protein homodimers, which have a reduced propensity to oligomerize as compared to unlinked fluorescent protein monomers, and to methods of making and using such non-oligomerizing tandem fluorescent proteins.

2. Background Information

The identification and isolation of fluorescent proteins in various organisms, including marine organisms, has provided a valuable tool to molecular biology. The green fluorescent protein (GFP) of the jellyfish *Aequorea victoria*, for example, has become a commonly used reporter molecule for examining various cellular process, including the regulation of gene expression, the localization and interactions of cellular proteins, the pH of intracellular compartments, and the activities of enzymes.

The usefulness of *Aequorea* GFP has led to the identification of numerous other fluorescent proteins in an effort to obtain proteins having different useful fluorescence characteristics. In addition, spectral variants of *Aequorea* GFP have been engineered, thus providing proteins that are excited or fluoresce at different wavelengths, for different periods of time, and under different conditions. The identification and cloning of a red fluorescent protein, dsRed, from *Discosoma* raised a great deal of interest due to its ability to fluoresce in the red wavelength. The availability of such fluorescent proteins has greatly expanded the studies that the proteins can be used for and, consequently, our understanding of cellular structure and function.

Although the availability of a wide variety of naturally occurring fluorescent proteins and spectral variants of the proteins has allowed for substantial advances, limitations to the use of fluorescent proteins remain. In particular, GFP and its spectral variants, as well as other naturally occurring fluorescent proteins such as dsRed have a propensity to self-associate under physiological conditions, thus forming dimers, tetramers, and the like. As such, it can be difficult in some cases to confirm whether a result is due, for example, to a specific interaction of two proteins under investigation, or whether a perceived interaction is an artifact caused by the oligomerization of fluorescent proteins linked to each of the two proteins under investigation.

Substantial progress has been made in designing mutants of GFP and its spectral variants that have substantially reduced oligomerizing activity. Progress also has been made in designing dsRed mutants that have a reduced propensity to form oligomers, and dsRed mutants that form only dimers have been developed. However, previous efforts to modify dsRed to prevent dimer formation have resulted in the formation of non-fluorescent proteins. Thus, a need exists for methods to reduce the propensity of red fluorescent proteins such as dsRed to self-associate. The present invention satisfies this need and provides additional advantages.

SUMMARY OF THE INVENTION

The present invention relates to a non-oligomerizing tandem fluorescent protein, ;which includes a first monomer of a fluorescent protein operatively linked to at least a second monomer of the fluorescent protein, wherein the propensity of the tandem fluorescent protein to oligomerize is reduced or inhibited as compared to a monomer of the fluorescent protein. The fluorescent protein of a non-oligomerizing tandem fluorescent protein can be a green fluorescent protein (GFP), a red fluorescent protein (RFP), or a fluorescent protein related to a GFP or an RFP.

In one embodiment, the fluorescent protein is a *Discosoma* RFP or a fluorescent protein related to a *Discosoma* RFP, for example, a DsRed protein having an amino acid sequence as set forth in SEQ ID NO: 12, or a mutant of SEQ ID NO:12, such as SEQ ID NO:12 having an I125R mutation. In another embodiment, the fluorescent protein is an *Aequorea* GFP, a *Renilla* GFP, a *Phialidium* GFP, or a fluorescent protein related to an *Aequorea* GFP, a *Renilla* GFP, and a *Phialidium* GFP, for example, a cyan fluorescent protein (CFP), or a yellow fluorescent protein (YFP), or a spectral variant of the CFP or the YFP, or an enhanced GFP (EGFP; SEQ ID NO: 4), an enhanced CFP (ECFP; SEQ ID NO: 6), an EYFP-V68L/Q69K (SEQ ID NO: 10), or an enhanced YFP (EYFP; SEQ ID NO: 8), each of which is related to *Aequorea* GFP. In still another embodiment, the fluorescent protein of a non-oligomerizing tandem fluorescent protein comprises a mutation of an amino acid residue corresponding to A206, L221, F223, or a combination thereof of SEQ ID NO: 2, for example, a mutation corresponding to an A206K mutation, an L221K mutation, an F223R mutation, or an L221K and F223R mutation of SEQ ID NO: 2, or a mutation corresponding to an A206K mutation, an L221K mutation, an F223R mutation, or an L221K and F223R mutation of SEQ ID NO: 6 or SEQ ID NO: 10.

The first monomer and at least second monomer of a non-oligomerizing tandem fluorescent protein are operatively linked such that an intramolecular oligomer is formed, thus reducing or inhibiting the propensity of the fluorescent protein to form intermolecular oligomers. The first and at least second monomer can be operatively linked using any bond or linker that does not disrupt the fluorescent property of the fluorescent protein. In one embodiment, the first and at least second monomer are operatively linked using a peptide linker, for example, the peptide linker has an amino acid sequence as set forth in SEQ ID NO:26. For example, the fluorescent protein can have an amino acid sequence as set forth in SEQ ID NO:12 and the peptide linker has an amino acid sequence as set forth in SEQ ID NO:26, or the fluorescent protein can have an amino acid sequence substantially as set forth in SEQ ID NO:12, including an I125R mutation, and the peptide linker has an amino acid sequence as set forth in SEQ ID NO:26. In another embodiment, the first and at least second monomer are operatively linked using a polynucleotide sequence, a peptidomimetic, or other synthetic linker, for example, a synthetic polymer.

A non-oligomerizing tandem fluorescent protein can further at least a third monomer of the fluorescent protein, which is operatively linked to the first monomer or the second monomer. The linkers for operatively linking the three or more monomers of a non-oligomerizing tandem fluorescent protein can be the same or different linkers.

The present invention also relates to a fusion protein, which includes a non-oligomerizing tandem fluorescent protein operatively linked to at least one polypeptide of interest. The non-oligomerizing tandem fluorescent protein can be linked to the polypeptide of interest using any linker or linkage, including, for example, a peptide bond, a peptide linker, or other linker molecule. The polypeptide of interest can be any polypeptide, including, for example, a peptide tag such as a polyhistidine peptide; a cellular polypeptide such as an enzyme, a G-protein, a growth factor receptor, or a transcription factor; or a reporter polypeptide, which provides a detectable signal or provides a means for isolating a fusion protein containing the reporter polypeptide. The polypeptide of interest also can be one of two or more proteins that associate to form a complex.

The present invention further relates to a kit, which contains at least one non-oligomerizing tandem fluorescent protein of the invention, and can contain a plurality of different non-oligomerizing tandem fluorescent proteins. If desired, one or more non-oligomerizing tandem fluorescent proteins of the kit can be a fusion protein.

The present invention also relates to a polynucleotide encoding a non-oligomerizing tandem fluorescent protein of the invention, as well as to a recombinant nucleic acid molecule, which includes a polynucleotide of the invention operatively linked to at least a second polynucleotide. The at least second polynucleotide can be, for example, a transcription or translation regulatory element, or can encode a polypeptide of interest, or can include a restriction endonuclease recognition site or a recombinase recognition site. Also provided are vectors, which contain a polynucleotide or recombinant nucleic acid molecule of the invention, as well as host cell, which contains such a polynucleotide or vector. In addition, a kit containing at least one polynucleotide or recombinant nucleic acid molecule of the invention is provided. In one embodiment, the kit contains a plurality of different polynucleotides or recombinant nucleic acid molecules or a combination thereof.

The present invention further relates to a tandem non-oligomerizing fluorescent protein, which includes a donor, comprising a first fluorescent protein, an acceptor, comprising a second fluorescent protein, and a peptide linker moiety operatively linking the donor and the acceptor. In such a tandem non-oligomerizing fluorescent protein, the first fluorescent protein and second fluorescent protein are different, and at least the first fluorescent protein or the second fluorescent protein is a non-oligomerizing tandem fluorescent protein of the invention. In addition, the cyclized amino acids of the donor emit light characteristic of the donor, and the donor and the acceptor exhibit fluorescence resonance energy transfer when the donor is excited, and the linker moiety does not substantially emit light to excite the acceptor.

In one embodiment, each of the first fluorescent protein and the second fluorescent protein is a non-oligomerizing tandem fluorescent protein in a tandem non-oligomerizing fluorescent protein of the invention. For example, the non-oligomerizing tandem fluorescent protein can be a *Discosoma* RFP or a fluorescent protein related to a *Discosoma* RFP, such as a DsRed protein having an amino acid sequence as set forth in SEQ ID NO: 12 or a mutant DsRed protein such as SEQ ID NO:12 containing an I125R mutation.

In another embodiment, the first fluorescent protein is a non-oligomerizing tandem fluorescent protein, and the second fluorescent protein is a non-oligomerizing fluorescent protein. The non-oligomerizing fluorescent protein can contain a mutation of an amino acid residue corresponding to A206, L221, F223, or a combination thereof of SEQ ID NO:2, for example, a mutation corresponding to S65G/S72A/T203Y/H231L in SEQ ID NO:2; a mutation corresponding to S65G/V68L/Q69K/S72A/T203Y/H231L in SEQ ID NO:2; a mutation corresponding to K26R/F64L/S65T/Y66W/N 146I/M153T/V163A/N164H/H231L in SEQ ID NO: 2; or a mutation corresponding to H148G in SEQ ID NO: 2.

The present invention also relates to a method for determining the pH of a sample. Such a method can be performed, for example, by contacting the sample with a first non-oligomerizing tandem fluorescent protein, wherein the emission intensity of the first non-oligomerizing tandem fluorescent protein changes as pH varies between pH 5 and pH 10, exciting the indicator; and determining the intensity of light emitted by the first non-oligomerizing tandem fluorescent protein at a first wavelength, wherein the emission intensity of the first non-oligomerizing tandem fluorescent protein indicates the pH of the sample. The sample can be any sample, including, for example, a biological tissue such as a cell or a fraction thereof.

A method of determining the pH of a sample can include contacting the sample with a non-oligomerizing fluorescent protein, which is different from the first non-oligomerizing tandem fluorescent protein, and wherein the emission intensity of the non-oligomerizing fluorescent protein changes as pH varies from 5 to 10, and emits at a second wavelength that is distinct from the first wavelength; exciting the non-oligomerizing fluorescent protein; determining the intensity of light emitted by the non-oligomerizing fluorescent protein at the second wavelength; and comparing the fluorescence at the second wavelength to the fluorescence at the first wavelength.

The non-oligomerizing fluorescent protein can be a second non-oligomerizing tandem fluorescent protein. In addition, the first non-oligomerizing tandem fluorescent protein, or the non-oligomerizing fluorescent protein, can contain a targeting sequence, for example, a cell compartmentalization domain, which can direct localization of the fluorescent protein in a cell to cytosol, endoplasmic reticulum, mitochondrial matrix, chloroplast lumen, medial trans-Golgi cisternae, a lumen of a lysosome, or a lumen of an endosome. In one embodiment, the targeting sequence is a cell compartmentalization includes amino acid residues 1 to 81 of human type II membrane-anchored protein galactosyltransferase, or amino acids 1 to 12 of the presequence of subunit IV of cytochrome c oxidase.

The present invention also relates to a method for determining whether a sample contains an enzyme. Such a method can be performed, for example, by contacting a sample with a tandem non-oligomerizing fluorescent protein; exciting the donor, and determining a fluorescence property in the sample, wherein the presence of the enzyme in the sample results in a change in the degree of fluorescence resonance energy transfer. Also provided is a method for determining the activity of an enzyme in a cell. Such a method can be performed, for example, by providing a cell that expresses a tandem non-oligomerizing tandem fluorescent protein, wherein the peptide linker moiety comprises a cleavage recognition amino acid sequence specific for the enzyme coupling the donor and the acceptor, exciting the donor, and determining the degree of fluorescence resonance energy transfer in the cell, wherein the presence of enzyme activity in the cell results in a change in the degree of fluorescence resonance energy transfer.

The present invention also relates to a method for identifying the presence of a molecule in a sample. Such a method can be performed, for example, by operatively linking a non-oligomerizing tandem fluorescent protein to the molecule, and detecting fluorescence due to the non-oligomerizing tandem fluorescent protein in a sample suspected of containing the molecule, thereby identifying the presence of the molecule in the sample. The molecule can be a polypeptide, for example, an antibody, an enzyme, or a receptor; a polynucleotide; or any other molecule of interest. The sample can be any sample, including, for example, a biological sample such as a cell, a tissue sample, or an extract of a cell or a tissue sample. As such, the detecting step can be performed on an intact cell or tissue sample. The non-oligomerizing tandem fluorescent protein can be operatively linked with the molecule under any conditions suitable for linking the protein to the molecule. For example, the protein and molecule can be operatively linked by expressing a recombinant nucleic acid molecule that encodes the non-oligomerizing tandem fluorescent protein and the molecule.

The present invention further relates to a method of identifying an agent or condition that regulates the activity of an expression control sequence. Such a method can be performed, for example, by exposing a recombinant nucleic acid molecule, which includes a polynucleotide encoding a non-oligomerizing tandem fluorescent protein operatively linked to an expression control sequence, to an agent or condition suspected of being able to regulate expression of a polynucleotide from the expression control sequence, and detecting fluorescence of the non-oligomerizing tandem fluorescent protein due to said exposing, thereby identifying an agent or conditions that regulates expression of the expression control sequence. The expression control sequence can be a transcription regulatory element, for example, a promoter, enhancer, silencer, or insulator, or can be a translation regulatory element, for example, an internal ribosome entry site. The agent or condition can be any agent or condition, including, for example, exposure to proteins expressed in a cell.

The present invention further relates to a method of identifying a specific interaction of a first molecule and a second molecule. Such a method can be performed, for example, by contacting the first molecule, which is operatively linked to a donor first non-oligomerizing tandem fluorescent protein, and the second molecule, which is operatively linked to an acceptor non-oligomerizing fluorescent protein, under conditions that allow a specific interaction of the first molecule and second molecule, wherein the first non-oligomerizing tandem fluorescent protein and the non-oligomerizing fluorescent protein are different; exciting the donor; and detecting fluorescence resonance energy transfer from the donor to the acceptor, thereby identifying a specific interaction of the first molecule and the second molecule. In such a method, the non-oligomerizing fluorescent protein can be a second non-oligomerizing tandem fluorescent protein, or can be any other non-oligomerizing fluorescent protein.

In one embodiment, the first molecule is a first cellular protein and the second molecule is a second cellular protein, wherein the first and second cellular proteins are the same or different. In another embodiment, the first molecule is a polynucleotide and the second molecule is a polypeptide, for example, a transcription regulatory element and a putative transcription factor.

The present invention also relates to a non-oligomerizing fluorescent protein, which contains at least one mutation that reduces or eliminates the ability of the fluorescent protein to oligomerize. The non-oligomerizing fluorescent protein can be derived from any fluorescent protein that is known to oligomerize, including, for example, a green fluorescent protein (GFP) such as an *Aequorea victoria* GFP, a *Renilla reniformis* GFP, a *Phialidium gregarium* GFP; a red fluorescent protein (RFP) such as a *Discosoma* RFP; or a fluorescent protein related to a GFP or an RFP. Thus, the non-oligomerizing fluorescent protein can be a cyan fluorescent protein (CFP), or a yellow fluorescent protein (YFP), enhanced GFP (EGFP), an enhanced CFP (ECFP), or an enhanced YFP (EYFP), or a variant of such fluorescent proteins, which can oligomerize but for the presence of one or more mutations that reduces or eliminates the propensity to oligomerize. Such a mutation can be, for example, a mutation of one or a combination of amino acid residues A206, L221 or F223 of *Aequorea* GFP (SEQ ID NO: 2), or a mutation of another fluorescent protein that corresponds to a mutation of A206, L221 or F223 of SEQ ID NO: 2. Such mutations are exemplified herein by the mutations A206K, L221K, F223R mutation, or L221K and F223R, of ECFP (SEQ ID NO: 6) and EYFP-V68L/Q69K (SEQ ID NO: 10), which are spectral variants of *Aequorea* GFP.

The present invention also relates to a fusion protein, which includes a non-oligomerizing fluorescent protein linked to one or more polypeptides of interest. The polypeptides of the fusion protein can be linked through peptide bonds, or the non-oligomerizing fluorescent protein can be linked to the polypeptide of interest through a linker molecule. A polypeptide of interest can be any polypeptide, including, for example, a peptide tag such as a polyhistidine peptide, or a cellular polypeptide such as an enzyme, a G-protein, a growth factor receptor, or a transcription factor; and can be one of two or more proteins that can associate to form a complex. In one embodiment, the fusion protein is a tandem non-oligomerizing fluorescent protein construct, which includes a donor non-oligomerizing fluorescent protein, an acceptor non-oligomerizing fluorescent protein, and a peptide linker moiety coupling said donor and said acceptor, wherein cyclized amino acids of the donor emit light characteristic of said donor, and wherein the donor and the acceptor exhibit fluorescence resonance energy transfer when the donor is excited, and the linker moiety does not substantially emit light to excite the donor.

The present invention further relates to a polynucleotide that encodes an non-oligomerizing fluorescent protein, as well as to a vector containing such a polynucleotide, and a host cell containing a polynucleotide or vector. In addition, the invention relates to a recombinant nucleic acid molecule, which includes a polynucleotide encoding a non-oligomerizing fluorescent protein operatively linked to one or more other polynucleotides. The one or more other polynucleotides can be, for example, a transcription regulatory element such as a promoter or polyadenylation signal sequence, or a translation regulatory element such as a ribosome binding site. Such a recombinant nucleic acid molecule can be contained in a vector, which can be an expression vector, and the nucleic acid molecule or the vector can be contained in a host cell.

The present invention also relates to kits containing one or more compositions of the invention, for example, one or a plurality of non-oligomerizing fluorescent proteins, which can be a portion of a fusion protein, or one or a plurality of polynucleotides that encode the proteins. A kit of the invention also can contain one or a plurality of recombinant nucleic acid molecules, which encode, in part, non-oligomerizing fluorescent proteins, which can be the same or different, and further include, for example, an operatively linked second polynucleotide containing or encoding a restriction endonuclease recognition site or a recombinase recognition site, or any polypeptide of interest.

The present invention further relates to a method for identifying the presence of a molecule in a sample. Such a method can be performed, for example, by linking a non-oligomerizing fluorescent protein to the molecule, and detecting fluorescence due to the non-oligomerizing fluorescent protein in a sample suspected of containing the molecule, thereby identifying the presence of the molecule in the sample. The molecule to be detected can be any molecule, including, for example, a polypeptide such as an antibody, an enzyme, or a receptor, or a polynucleotide. In addition, the sample can be any sample, including a biological sample such as a cell, which can be a cell in culture or a cell isolated from an organism, a tissue sample, or an extract of a cell or a tissue sample. In one embodiment, the method is performed using an intact cell or tissue sample, wherein the presence of a molecule of interest in living cells can be identified.

Linking of the non-oligomerizing fluorescent protein to the molecule can be performed using an linkage that is stable under the conditions to which the polypeptide-molecule complex is to be exposed, and can be performed using a chemical reaction or can result of expression of a recombinant nucleic acid molecule encoding the linked complex. Thus, linking can be performed by contacting the non-oligomerizing fluorescent protein with the molecule under conditions suitable for linking the protein to the molecule, such conditions depending, for example, on the chemical nature of the molecule and the type of linkage desired, which can be a direct linkage or can be mediated by a linker moiety. Where the molecule is a polypeptide, linking can be performed by expressing a recombinant nucleic acid molecule comprising a polynucleotide encoding the non-oligomerizing fluorescent protein operatively linked to a polynucleotide encoding the molecule.

The present invention also relates to a method of identifying an agent or condition that regulates the activity of an expression control sequence. Such a method can be performed, for example, by exposing a recombinant nucleic acid molecule, which includes a polynucleotide encoding a non-oligomerizing fluorescent protein operatively linked to an expression control sequence, to an agent or condition suspected of being able to regulate expression of a polynucleotide from the expression control sequence, and detecting fluorescence of the non-oligomerizing fluorescent protein due to such exposure, thereby identifying an agent or conditions that regulates expression of the expression control sequence. The expression control sequence can be any such sequence, including, for example, a transcription regulatory element such as a promoter or a translation regulatory element such as a ribosome binding site. In addition, the agent can be any agent, including, for example, a peptide, polynucleotide, small organic molecule or the like. Similarly, the condition can be any condition, including, for example, exposure to proteins expressed in a cell and, therefore, the method can be used to identify a transcription factor, a translation factor, or the like, including tissue-specific factors.

The present invention also relates to a method of identifying a specific interaction of a first molecule and a second molecule. Such a method can be performed, for example, by contacting the first molecule, which is linked to a donor first non-oligomerizing fluorescent protein, and the second molecule, which is linked to an acceptor second non-oligomerizing fluorescent protein, under conditions that allow a specific interaction of the first molecule and second molecule; exciting the donor; and detecting fluorescence resonance energy transfer from the donor to the acceptor, thereby identifying a specific interaction of the first molecule and the second molecule. The first and second molecule can be cellular proteins, which are the same or different, or can be a polynucleotide and a polypeptide, thus providing, for example, a means to identify proteins that specifically interact such as proteins involved in transducing an intracellular signal, or to identify a transcription regulatory element that specifically binds a transcription factor.

The present invention also relates to a method for determining whether a sample contains an enzyme. Such a method can be performed, for example, by contacting a sample with a tandem non-oligomerizing fluorescent protein construct of the invention; exciting the donor, and determining a fluorescence property in the sample, wherein the presence of an enzyme in the sample results in a change in the degree of fluorescence resonance energy transfer. Similarly, the present invention relates to a method for determining the activity of an enzyme in a cell. Such a method can be performed, for example, providing a cell that expresses a tandem non-oligomerizing fluorescent protein construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

The present invention further relates to a method for determining the pH of a sample. Such a method can be performed, for example, by contacting the sample with a first non-oligomerizing fluorescent protein, wherein the emission intensity of the first non-oligomerizing fluorescent protein changes as pH varies between pH 5 and pH 10; exciting the indicator; and determining the intensity of light emitted by the first non-oligomerizing fluorescent protein at a first wavelength, wherein the emission intensity of the first non-oligomerizing fluorescent protein indicates the pH of the sample. The first non-oligomerizing fluorescent protein useful in this method, or in any method of the invention, can have an amino acid sequence of SEQ ID NO: 2, or a sequence substantially identical thereto, for example, having the mutations S65G/S72A/T203Y/H231L with respect to SEQ ID NO: 2, or having the mutations S65G/V68L/Q69K/S72A/T203Y/H231L with respect to SEQ ID NO: 2; or having the mutations K26R/F64L/S65T/Y66W/N146I/M153T/V163A/N164H/H231L with respect to SEQ ID NO: 2; or any of the above non-oligomerizing fluorescent protein further having a mutation corresponding to H148G or H148Q with respect to SEQ ID NO: 2.

The sample used in a method for determining the pH of a sample can be any sample, including, for example, a biological tissue sample, or a cell or a fraction thereof. In addition, the method can further include contacting the sample with a second non-oligomerizing fluorescent protein, wherein the emission intensity of the second non-oligomerizing fluorescent protein changes as pH varies from 5 to 10, and wherein the second non-oligomerizing fluorescent protein emits at a second wavelength that is distinct from the first wavelength; exciting the second non-oligomerizing fluorescent protein; determining the intensity of light emitted by the second non-oligomerizing fluorescent protein at the second wavelength; and comparing the fluorescence at the second wavelength to the fluorescence at the first wavelength. The first (or second) non-oligomerizing fluorescent protein can include a targeting sequence, for example, a cell compartmentalization domain such a domain that targets the non-oligomerizing fluorescent protein in a cell to the cytosol, the endoplasmic reticulum, the mitochondrial matrix, the chloroplast lumen, the medial trans-Golgi cisternae, a lumen of a lysosome, or a lumen of an endosome. For example, the cell compartmentalization domain can include amino acid residues 1 to 81 of human type II membrane-anchored protein galactosyltransferase, or amino acid residues 1 to 12 of the presequence of subunit IV of cytochrome c oxidase.

DETAILED DESCRIPTION OF THE INVENTION

Figure 1:
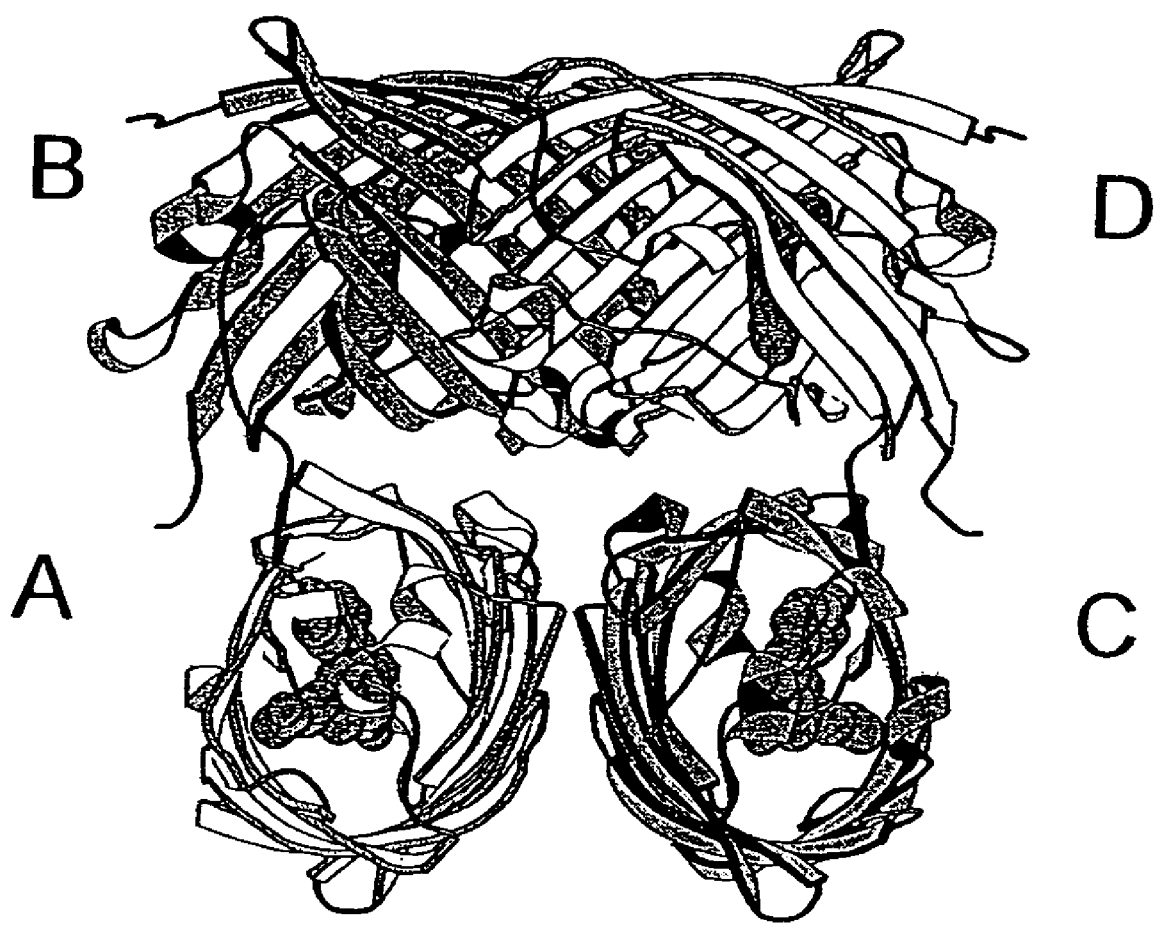
FIG. 1 illustrates the tetrameric form of DsRed (PDB identification code 1G7K). The A-C and B-D interfaces are equivalent, as are the A-B and C-D interfaces. The labeling of the subunits is arbitrary and, therefore, the convention used in this FIGURE differs from 1G7K, but is consistent with the PDB submission 1GGK.

The present invention provides non-oligomerizing fluorescent proteins, which are derived from fluorescent proteins that can oligomerize. As disclosed herein, a non-oligomerizing fluorescent protein of the invention can be derived from a naturally occurring fluorescent protein or from a spectral variant or mutant thereof, and contains at least one mutation that reduces or eliminates the ability of the fluorescent protein to oligomerize.

A non-oligomerizing fluorescent protein of the invention can be derived from any fluorescent protein that is known to oligomerize, including, for example, a green fluorescent protein (GFP) such as an *Aequorea victoria* GFP, a *Renilla reniformis* GFP, a *Phialidium gregarium* GFP; a red fluorescent protein (RFP) such as a *Discosoma* RFP; or a fluorescent protein related to a GFP or an RFP. Thus, the non-oligomerizing fluorescent protein can be a cyan fluorescent protein (CFP), a yellow fluorescent protein (YFP), an enhanced GFP (EGFP; SEQ ID NO: 4), an enhanced CFP (ECFP; SEQ ID NO: 6), an enhanced YFP (EYFP; SEQ ID NO: 8), a DsRed fluorescent protein (SEQ ID NO: 12), or a mutant or variant of such fluorescent proteins.

As disclosed herein, the propensity of the non-oligomerizing fluorescent proteins of the invention to oligomerize is reduced or eliminate. In one embodiment, the propensity of a non-oligomerizing fluorescent protein to oligomerize is reduced or eliminated due to operatively linking a first monomer of a fluorescent protein to at least a second monomer of the fluorescent protein, thereby forming an intramolecular 'dimer', 'trimer' or the like. Such operatively linked homopolymers, which are referred to herein as "non-oligomerizing tandem dimers," have a substantially reduced ability to form intermolecular oligomers. Such non-oligomerizing tandem fluorescent proteins are exemplified herein by two monomers of DsRed (SEQ ID NO:12) operatively linked by a peptide linker (SEQ ID NO:26), and by two monomers of a mutant DsRed, which has an amino acid sequence of SEQ ID NO:12, and including an I125R mutation, operatively linked by the peptide linker of SEQ ID NO:26.

In another embodiment, the propensity of a non-oligomerizing fluorescent protein to oligomerize is reduced or eliminated due to the presence of one or more mutations in the fluorescent protein. Such mutations are exemplified by a mutation of one or a combination of amino acid residues A206, L221 or F223 of *Aequorea* GFP (SEQ ID NO: 2), or a mutation of another fluorescent protein that corresponds to a mutation of A206, L221 or F223 of SEQ ID NO: 2, for example, by the mutations A206K, L221K, F223R of GFP (SEQ ID NO:2), or by the mutations L221K and F223R of ECFP (SEQ ID NO: 6) and EYFP-V68L/Q69K (SEQ ID NO: 10), which are spectral variants of *Aequorea* GFP.

As used herein, the term "non-oligomerizing tandem fluorescent protein" refers to a composition of two or more monomers of a fluorescent protein that are operatively linked and that exhibit a characteristic fluorescence emission spectrum and fluorescence excitation spectrum. As disclosed herein, the intramolecular 'oligomerization' characteristic of a non-oligomerizing tandem fluorescent protein of the invention reduces or eliminates the propensity of fluorescent protein to undergo intermolecular oligomerization.

The term "non-oligomerizing fluorescent protein" is used more broadly herein to refer to fluorescent proteins that have been modified such that they have a reduced propensity to oligomerize as compared to a corresponding unmodified fluorescent protein. As such, unless specifically indicated otherwise, the term "non-oligomerizing fluorescent protein" encompasses non-oligomerizing tandem fluorescent proteins, as well as fluorescent proteins that contain one or more mutations that reduce or eliminate the propensity of the fluorescent protein to oligomerize.

The term "tandem non-oligomerizing fluorescent protein" is used herein to refer to a composition containing two different fluorescent proteins, including a donor fluorescent protein operatively linked to an acceptor fluorescent protein, wherein at least one of the fluorescent proteins is a non-oligomerizing fluorescent protein. As such, with respect to its fluorescent protein components, a "tandem non-oligomerizing fluorescent protein" can be analogized to a heteropolymer, whereas a "non-oligomerizing tandem fluorescent protein" can be analogized to a homopolymer.

*Aequorea* GFP is widely used in cell biology as a protein module that can be fused to host proteins to make the latter fluorescent (Tsien, *Ann. Rev. Biochem.* 67:509-544, 1998, which is incorporated herein by reference). For example, GFP is commonly used to characterize subcellular localization and trafficking properties of proteins, to which the GFP is fused. In addition, spectral variants of GFP, including CFP and YFP and variants thereof have been used to measure the associative properties of host proteins by fluorescence resonance energy transfer (FRET). FRET between CFP and YFP also has been exploited to create biosensors for calcium ion, and to determine the associative properties of growth factor receptors and G protein-coupled receptors.

The GFP spectral mutants, CFP and YFP and variants thereof such as ECFP (SEQ ID NO: 6) and EYFP-V68L/Q69K (SEQ ID NO: 10), have most of the desirable properties required of good FRET partners, except that these proteins exhibit homoaffinity and form dimers. As such, GFP and its spectral variants, show distinct tendencies to dimerize in some crystal structures, in solution, and in many conditions inside cells. Such dimerization means that host proteins fused to a GFP (or variant) can be induced to dimerize, thereby perturbing their functions and resulting in artifacts when FRET between different colors of GFP spectral variants is used to assess protein-protein interaction. Accordingly, it would be desirable to identify mutations that can eliminate the tendency of all colors of GFP spectral variants to dimerize, without having any deleterious effects on other properties of the fluorescent proteins. As disclosed herein, the mutations, A206K, L221K and F223R, either alone or in combinations, in ECFP (SEQ ID NO: 6) and EYFP-V68L/Q69K (SEQ ID NO: 10) reduce or eliminate the propensity of GFP and its spectral variants to dimerize. Thus, except where dimerization is positively desired, one or more of these mutations can be routinely incorporated into a GFP variant, thereby reducing or eliminating its ability to induce artifactual dimerization.

Although *Aequorea* GFP has proven to be a tool of great value to cell biologists, the propensity of GFP to dimerize at relatively low expression levels in cells has limited the development of new and better assays, particularly assays for the localization of host proteins and the determination of their associative properties. The present invention provides a means to substantially reduce or eliminate the ability of fluorescent proteins such as GFP to oligomerize, thereby solving the problems associated therewith, and allowing the development of assays that could not previously be performed.

Another limitation is that, while GFP variants with blue, cyan, and yellowish green emissions have been engineered, all have emission maxima shorter than 529 nm. Recently, polynucleotides encoding six anthozoan (coral) fluorescent proteins having 26% to 30% identity to *Aequorea* GFP (SEQ ID NO: 2) were cloned by Matz et al. (*Nature Biotechnol.* 17:969-973, 1999, which is incorporated herein by reference). Although most of the coral fluorescent proteins had emission maxima within the range covered by GFP or its variants, one coral protein, drFP583 ("DsRed"; SEQ ID NO: 12), which was isolated from a red portion of a *Discosoma* species, had excitation and emission maxima at 558 and 583 nm, respectively, the longest yet reported for a wild type spontaneously fluorescent protein (Matz et al., supra, 1999). Despite the relatively modest sequence identity to GFP, enough sequence similarity was conserved to suggest that the coral proteins would form 11-stranded 9-barrels, similar to that of GFP. In addition, the two important residues contributing to the chromophore of GFP, Tyr66 and Gly67, and some of the important polar residues contacting the chromophore such as Arg96 and Glu222, were conserved in the coral proteins. In DsRed, the amino acids corresponding to these GFP residues are numbered Tyr67, Gly68, Arg95, and Glu215, respectively, and additional amino acids that can be involved in oligomerization can be identified using X-ray crystallography methods (see Example 3).

The cloning of a red fluorescent protein (DsRed) from *Discosoma* raised a great deal of interest due to its tremendous potential as a tool for the advancement of cell biology. However, a careful investigation of the properties of this protein revealed several problems that would preclude DsRed from being as widely accepted as the *Aequorea* GFP and its blue, cyan, and yellow variants, which have found widespread use as both genetically encoded indicators for tracking gene expression and as donor/acceptor pairs for fluorescence resonance energy transfer (FRET). Extending the spectrum of available colors to red wavelengths would provide a distinct new label for multicolor tracking of fusion proteins and together with GFP would provide a new FRET donor/acceptor pair that would be superior to the currently preferred cyan/yellow pair.

The two most pressing problems with the 28 kDa DsRed are its strong tendency to oligomerize and its slow maturation. A variety of techniques have been used to determine that DsRed is an obligate tetramer both in vitro and in vivo. For numerous reasons, the oligomeric state of DsRed is problematic for applications in which it is fused to a protein of interest in order to monitor trafficking or interactions of the latter. Using purified protein, it was shown that DsRed requires greater than 48 hours to reach >90% of its maximal red fluorescence (see below). During the maturation process, a green intermediate initially accumulates and is slowly converted to the final red form. However, the conversion of the green component does not proceed to completion and thus a fraction of aged DsRed remains green. The primary disadvantage of the incomplete maturation is an excitation spectrum that extends well into the green wavelengths due to energy transfer between the green and red species within the tetramer. This is a particularly serious problem due to overlap with the excitation spectra of potential FRET partners such as GFP.

The original report of the cloning of DsRed provided an in vivo application marking the fates of *Xenopus* blastomeres after 1 week of development (Matz et al., supra, 1999). As disclosed herein, DsRed has been characterized with respect to the time the red fluorescence takes to appear, the pH sensitivity of the chromophore, how strongly the chromophore absorbs light and fluoresces, how readily the protein photobleaches, and whether the protein normally exists as a monomer or an oligomer in solution (see Example 2). The results demonstrate that DsRed provides a useful complement to or alternative for GFP and its spectral mutants. In addition, DsRed mutants that are non-fluorescent or that are blocked or slowed in converting from green to red emission were characterized, including mutants in which the eventual fluorescence is substantially red-shifted from wild type DsRed (see Example 2; see, also, Baird et al., *Proc. Natl. Acad. Sci., USA* 97:11984-11989, 2000; Gross et al., *Proc. Natl. Acad. Sci., USA* 97:11990-11995, 2000, each of which is incorporated herein by reference).

As disclosed herein, mutations were introduced into DsRed similar to those introduced into the GFP spectral variants, and DsRed mutants having reduced oligomerization activity were identified, including, for example, a DsRed-I125R mutant of DsRed as set forth in SEQ ID NO: 12 (see Example 3). The strategy for producing the DsRed mutants involved introducing mutations in DsRed that were predicted to interfere with the dimer interfaces (A-B or A-C, see FIG. 1) and thus prevent formation of the tetramer. This strategy resulted in the production of DsRed mutants that had a reduced propensity to form tetramers by disrupting the A-C interface, for example, using the single replacement of isoleucine 125 with an arginine (I125R).

The A-B interface proved to be more resilient, and mutations that potentially could disrupt this interface were ineffective and resulted in non-fluorescent proteins. As disclosed herein, a novel approach was used to overcome the intermolecular oligomerization propensity of DsRed by linking the C-terminus of the A subunit to the N-terminus of the B subunit through a flexible tether to produce tandem dimers. Based on the crystal structure of DsRed, an 18 residue linker (Whitlow et al., *Prot. Eng.* 6:989-995, 1993, which is incorporated herein by reference) was predicted to be long enough to extend from the C-terminus of the A subunit to the N-terminus of the B subunit (about 30 Å), but not from the N-terminus of the C subunit (greater than 70 Å). As such, 'oligomerization' in the tandem dimers is intramolecular, i.e., the tandem dimer of DsRed (tDsRed), for example, is encoded by a single polypeptide chain. Furthermore, a combination of tDsRed with the I125R mutant (tDsRed-I125R) resulted in a monomeric red fluorescent protein that effectively solved the oligomer problem (Example 4). It should be recognized that this strategy can be generally applied to any protein system in which the distance between the N-terminus of one protein and the C-terminus of a dimer partner is known, such that a linker having the appropriate length can be used to operatively link the monomers. In particular, this strategy can be useful for other modifying other fluorescent proteins that have interesting spectral properties, but form obligate dimers that are difficult to disrupt using the targeted mutagenesis method disclosed herein.

The availability of a wide range of variously-colored "spectral mutants" of GFP has provided a potential means for monitoring the associative properties of proteins via FRET. FRET is a quantum mechanical phenomenon of radiation-less energy transfer between two fluorophores, that is dependent on the proper spectral overlap of a donor and an acceptor, their distance from each other, and the relative orientation of the chromophores' transition dipoles. Using standard molecular biology technology, fusions can be generated between proteins of interest and spectral mutants of fluorescent proteins, which can then serve effectively as donor and acceptor FRET partners. As indicated above, the GFP spectral mutants have most of the requisite properties to serve as useful FRET partners, except for their homoaffinity and propensity for dimerization. Thus, while the number of FRET-based assays using GFP and its variants is increasing (see, for example, Mitra et al., Gene 173:13-17, 1996; Hartman and Vale, Science 286:782-785, 1999; Zacharias et al., Curr. Opin. Neurobiol. 10:416-421, 2000), the propensity of the GFP-related fluorescent proteins to associate with each other can complicate characterization of protein associations reported by FRET, which should be due solely to interactions of the proteins with no participation from the fluorophore to which they are linked.

FRET assays using GFP spectral variants can fail because dimerization can mask or mimic host protein interactions such that the data cannot be interpreted. Changes in FRET can be masked, for example, when dimerization of a CFP or YFP supersedes or prevents a conformational change of an intervening peptide or protein, or when dissociation of two or more host proteins is not allowed or is impeded due to dimerization of the fluorescent proteins. Similarly, if a CFP and YFP are present in a single fusion protein, a dimer interaction between these proteins can result, eliminating the ability to detect a change that may have occurred within a single fusion protein, similar to the hypothesized oligomerization of chameleons. Thus, situations where changes in FRET are mimicked can occur when dimerization of the GFPs or GFP spectral mutants mimic an interaction that otherwise is believed to be occurring between two host proteins.

In addition to interfering with FRET analysis, oligomerization of fluorescent proteins such as DsRed, GFP and its variants causes other problems that limit its usefulness. For example, another important and common application of these proteins is as a fluorescent label for observing, in living cells, the subcellular localization or distribution of proteins to which the fluorescent protein has been fused. Depending on the localization and naturally-occurring oligomeric state of the protein to which the fluorescent protein is fused, the fluorescent proteins can reach a local concentration in a cell in excess of that required for dimerization, thus altering the spatial distribution or function of its fusion partner.

It is difficult to determine in advance whether any of the problems associated with dimerization of fluorescent marker proteins will invalidate the results of a particular assay. However, mimicking of an intramolecular interaction where none exists, for example, FRET between a CFP and a YFP fused to two separate proteins, can occur when the fluorescent proteins are targeted to various subcellular locations such as the plasma membrane (PM), or even when expressed free in the cytoplasm (Miyawaki and Tsien, Meth. Enzymol. 327:472-500, 2000, which is incorporated herein by reference). Since such artifacts can be difficult to detect and prove, it would a great advantage if dimerization of the fluorescent proteins can be avoided. As disclosed herein, the present invention provides a means to substantially reduce or eliminate the propensity of fluorescent proteins to dimerize, thereby enabling accurate monitoring of the associative properties and distributions of host proteins in a cell, including erroneous FRET caused by fluorescent protein oligomerization, as well as other problems such as protein localization associated with such oligomerization.

The crystal structures of GFP and several of its variants have been solved (see, for example, Ormo et al., Science 273:1392-1395, 1996; Yang et al., Nature Biotechnol. 14:1246-1251, 1996; Wachter et al., Biochemistry 36:9759-9765, 1997; Palm et al., Nature Struct. Biol. 4:361-365, 1997, each of which is incorporated herein by reference). Depending on the experimental conditions used to form the crystal, the crystallographic unit cell is a head-to-tail, side-by-side dimer (Phillips, In "Green Fluorescent Protein: Properties, Applications and Protocols" (eds. Chalfie and Kain 1998), pages 77-96, which is incorporated herein by reference; see, also, Yang et al, supra, 1996; Tsien, supra, 1998). In order to form crystals, GFP must be very concentrated. As such, the structure of GFP in a crystal may not represent the state of the protein in solution. However, other lines of evidence indicate that GFP and its variants can form dimers in solution and that dimerization can occur at the concentrations and conditions that commonly exist in a cell-biological context (Ward et al., In "Green Fluorescent Protein: Properties, Applications and Protocols" (eds. Chalfie and Kain 1998), pages 45-75, which is incorporated herein by reference; see, also, Phillips, supra, 1998).

Contact sites identified in one crystal structure included a core of hydrophobic side chains from each of the two monomers and potentially many hydrophilic contacts (Yang et al., supra, 1996). This patch of hydrophobic side chains has been suggested to play a role in the association of GFP with the $Ca^{2+}$-sensitive photoprotein, aequorin in the jellyfish. Residues A206, L221 and F223 appeared to be reasonable candidates for creating the contacts between monomers when GFP is in solution or expressed exogenously in cells (Yang et al., supra, 1996; Phillips, supra, 1998). In order to determine whether one or more of these residues affect dimerization under physiological conditions, mutations that substituted amino acid residues having positively charged side chains were introduced and the interactions between the mutagenized monomers was examined. A quantitative determination of dimer affinity was made by subjecting highly purified ECFP (SEQ ID NO: 6) and EYFP-V68L/Q69K (SEQ ID NO: 10), and "dimer mutants" derived therefrom, to analytical ultracentrifugation, which can very accurately determine the degree of association between self associating proteins (McRorie and Voelker, In "Self-associating systems in the analytical ultracentrifuge (Beckman Instruments 1993)). Similarly, ECFP (SEQ ID NO: 6) and EYFP-V68L/Q69K (SEQ ID NO: 10) targeted to the plasma membrane, and dimer mutants derived from these GFP variants, were used in cell biological experiments designed specifically to determine the self-associative behavior of the various proteins.

As disclosed herein, amino acid residues A206, L221 and F223 of a GFP (see, for example, SEQ ID NO: 2) are sufficient to induce dimerization of GFP and spectral variants thereof at relatively low concentrations in solution and in living cells, and mutations of A206, L221 and F223, alone or in combination, to positively-charged residues substantially reduced or eliminated the interaction of the monomers in solution and in living cells. Since ECFP (SEQ ID NO: 6) and EYFP-V68L/Q69K (SEQ ID NO: 10), and virtually all other GFP-related mutants, have the same residue composition at these three positions as the wild type GFP (Prasher et al., *Gene* 111:229-233, 1992, which is incorporated herein by reference), the present results indicate that corresponding mutations in other fluorescent proteins having substantially the same general structure, including GFP spectral variants and the RFP, DsRed, similarly can reduce or eliminate the ability of the proteins to oligomerize (see Examples 1 and 3).

Other *Aequorea* GFP-related fluorescent proteins that can be modified according to a method of the invention so as to reduce or eliminate the propensity to oligomerize are well known in the art, and are exemplified by those having the mutations F64L, S65T, Y66W, F99S, or V163A, wherein the amino acid residues are referred to with respect to SEQ ID NO: 2, including variants thereof as disclosed in International Publ. No. WO 00/71565 A2, published Nov. 30, 2000, which is incorporated herein by reference. The numbering of the GFP amino acids as referred to herein conforms to that in native *Aequorea* GFP (SEQ ID NO: 2), wherein the first serine is amino acid number 2 even if a valine (amino acid no. 1a) has been inserted to optimize ribosome initiation. For example, F64L refers to a substitution of leucine for phenylalanine at amino acid position 64 following the initiating methionine.

Examples of GFP spectral variants in addition to CFP and YFP, include, for example, enhanced GFP (EGFP; SEQ ID NO: 4; F64L/S65T/H231L); EYFP (SEQ ID NO: 8; S65G/S72A/T203Y/H231L); EYFP-V68L/Q69K (SEQ ID NO: 10; S65G/V68L/Q69K/S72A/T203Y/H231L); ECFP (SEQ ID NO: 6; K26R/F64L/S65T/Y66W/N146I/M153T/V163A/N164H/H231L), and the like; and variants of these GFP-related fluorescent proteins having the mutation H148G or H148Q, wherein the indicated mutations are with respect to SEQ ID NO: 2 (see International Publ. No. WO 00/71565 A2, supra, 2000). Additional examples of fluorescent proteins that can be modified to reduce or eliminate the propensity to oligomerize include DsRed and variants thereof, which, as disclosed herein, can have desirable fluorescent characteristics as compared to native DsRed (see Examples 2 and 3), yellow fluorescent protein from *Vibrio fischeri* strain Y-1, Peridinin-chlorophyll a binding protein from the dinoflagellate *Symbiodinium phycobiliproteins* from marine cyanobacteria such as *Synechococcus*, for example, phycoerythrin and phycocyanin, or oat phytochromes from oat reconstructed with phycoerythrobilin (see Baldwin, *Biochemistry* 29:5509-5515, 1990; Morris et al., *Plant Mol. Biol.* 24:673-677, 1994; Wilbanks et al., *J. Biol. Chem.* 268:1226-1235, 1993; Li et al., *Biochemistry* 34:7923-7930, 1995; Murphy and Lagarias, *Curr. Biol.* 7: 870-876, 1997, each of which is incorporated herein by reference).

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a non-oligomerizing fluorescent protein of the invention linked to a polypeptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit W of cytochrome c oxidase (see, also, Hancock et al., *EMBO J.* 10:4033-4039, 1991; Buss et al., *Mol. Cell. Biol.* 8:3960-3963, 1988; U.S. Pat. No. 5,776,689, each of which is incorporated herein by reference).

The term "operatively linked" also is used in reference to the monomeric fluorescent protein components of a non-oligomerizing tandem fluorescent protein of the invention, as well as to components of a fusion protein comprising a non-oligomerizing fluorescent protein, including a non-oligomerizing tandem fluorescent protein, and polypeptide of interest. With respect to a non-oligomerizing tandem fluorescent protein, the term "operatively linked" means that the non-oligomerizing tandem fluorescent protein has a characteristic fluorescence emission and excitation spectra. The fluorescence emission and excitation spectra of the non-oligomerizing tandem fluorescent protein can be the same as the spectra of the monomeric form of the fluorescent protein comprising the non-oligomerizing tandem fluorescent protein, or the spectra can be different from those of the monomeric fluorescent protein. With respect to a fusion protein comprising a non-oligomerizing fluorescent protein, the term "operatively linked" means that the polypeptide components of the fusion protein are linked such that each maintains its function, including the fluorescence characteristics of the non-oligomerizing fluorescent protein and any function characteristic or of particular interest of the polypeptide linked thereto. The term "operatively linked" similarly is used herein to refer to the components of a tandem non-oligomerizing fluorescent protein of the invention, which comprises a first non-oligomerizing fluorescent protein, which can be a non-oligomerizing tandem fluorescent protein, and a second fluorescent protein, which can, but need not be a non-oligomerizing fluorescent protein, wherein the first fluorescent protein and second fluorescent protein are linked such that each maintains its fluorescence activity.

The term "oligomer" refers to a complex formed by the specific interaction of two or more polypeptides. A "specific interaction" or "specific association" is one that is relatively stable under specified conditions, for example, physiologic conditions. Reference to a "propensity" of proteins to oligomerize indicates that the proteins can form dimers, trimers, tetramers, or the like under specified conditions. Generally, fluorescent proteins such as GFPs and DsRed have a propensity to oligomerize under physiologic conditions although, as disclosed herein, fluorescent proteins also can oligomerize, for example, under pH conditions other than physiologic conditions. The conditions under which fluorescent proteins oligomerize or have a propensity to oligomerize can be determined using well known methods as disclosed herein (see Examples 1 and 3) or otherwise known in the art.

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound. The term "label" refers to a composition that is detectable with or without the instrumentation, for example, by visual inspection, spectroscopy, or a photochemical, biochemical, immunochemical or chemical reaction. Useful labels include, for example, phosphorus-32, a fluorescent dye, a fluorescent protein, an electron-dense reagent, an enzymes (such as is commonly used in an ELISA), a small molecule such as biotin, digoxigenin, or other haptens or peptide for which an antiserum or antibody, which can be a monoclonal antibody, is available. It will be recognized that a non-oligomerizing fluorescent protein of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and isolation of the expressed protein, respectively. A label useful for purposes of the present invention generally generates a measurable signal such as a radioactive signal, fluorescent light, enzyme activity, and the like, either of which can be used, for example, to quantitate the amount of the non-oligomerizing fluorescent protein in a sample.

The term "nucleic acid probe" refers to a polynucleotide that binds to a specific nucleotide sequence or sub-sequence of a second (target) nucleic acid molecule. A nucleic acid probe generally is a polynucleotide that binds to the target nucleic acid molecule through complementary base pairing. It will be understood that a nucleic acid probe can specifically bind a target sequence that has less than complete complementarity with the probe sequence, and that the specificity of binding will depend, in part, upon the stringency of the hybridization conditions. A nucleic acid probes can be labeled as with a radionuclide, a chromophore, a lumiphore, a chromogen, a fluorescent protein, or a small molecule such as biotin, which itself can be bound, for example, by a streptavidin complex, thus providing a means to isolate the probe, including a target nucleic acid molecule specifically bound by the probe. By assaying for the presence or absence of the probe, one can detect the presence or absence of the target sequence or sub-sequence. The term "labeled nucleic acid probe" refers to a nucleic acid probe that is bound, either directly or through a linker molecule, and covalently or through a stable non-covalent bond such as an ionic, van der Waals or hydrogen bond, to a label such that the presence of the probe can be identified by detecting the presence of the label bound to the probe.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "antibody" refers to a polypeptide substantially encoded by an immunoglobulin gene or immunoglobulin genes, or antigen-binding fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist as intact immunoglobulins and as well characterized antigen-binding fragments of an antibody, which can be produced by digestion with a peptidase or can using recombinant DNA methods. Such antigen-binding fragments of an antibody include, for example, Fv, Fab' and F(ab)'$_2$ fragments. The term "antibody," as used herein, includes antibody fragments either produced by the modification of whole antibodies or those synthesized de novo using recombinant DNA methodologies. The term "immunoassay" refers to an assay that utilizes an antibody to specifically bind an analyte. An immunoassay is characterized by the use of specific binding properties of a particular antibody to isolate, target, and/or quantify the analyte.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well known algorithm (see, for example, Meyers and Miller, *Comp. Appl. Biol. Sci.* 4:11-17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444 (1988); Higgins and Sharp, *Gene* 73:237-244, 1988; Higgins and Sharp, *CABIOS* 5:151-153; 1989; Corpet et al., *Nucl. Acids Res.* 16:10881-10890,1988; Huang, et al., *Comp. Appl. Biol. Sci.* 8:155-165, 1992; Pearson et al., *Meth. Mol. Biol.* 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a non-oligomerizing fluorescent protein also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gin, Q);
4) Arginine (Arg, R), Lysine (Lys, K);
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The Tm is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gln (CAG); His (CAC); and Pro (CCC).

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize $R_O$, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild type Aequorea GFP and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, which fluoresce when exposed to ultraviolet light, are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of Aequorea GFP can be derived from the naturally occurring GFP by engineering mutations such as amino acid substitutions into the reference GFP protein. For example ECFP is a spectral variant of GFP that contains substitutions with respect to GFP (compare SEQ ID NOS: 2 and 6).

Many cnidarians use green fluorescent proteins as energy transfer acceptors in bioluminescence. The term "green fluorescent protein" is used broadly herein to refer to a protein that fluoresces green light, for example, Aequorea GFP (SEQ ID NO: 2). GFPs have been isolated from the Pacific Northwest jellyfish, Aequorea victoria, the sea pansy, Renilla renifonnis, and Phialidium gregarium (Ward et al., Photochem. Photobiol. 35:803-808, 1982; Levine et al., Comp. Biochem. Physiol. 72B:77-85, 1982, each of which is incorporated herein by reference). Similarly, reference is made herein to "red fluorescent proteins", which fluoresce red, "cyan fluorescent proteins," which fluoresce cyan, and the like. RFPs, for example, have been isolated from the coral, Discosoma (Matz et al., supra, 1999).

A variety of Aequorea GFP-related fluorescent proteins having useful excitation and emission spectra have been engineered by modifying the amino acid sequence of a naturally occurring GFP from A. Victoria (see Prasher et al., Gene 111:229-233, 1992; Heim et al., Proc. Natl. Acad. Sci., USA 91:12501-12504, 1994; U.S. Ser. No. 08/337,915, filed Nov. 10, 1994; International application PCT/US95/14692, each of which is incorporated herein by reference). As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 85% sequence identity with the reference fluorescent protein, and particularly has a contiguous sequence of at least about 200 amino acids that shares at least about 95% sequence identity with the reference fluorescent protein. Thus, reference is made herein to an "Aequorea-related fluorescent protein" or to a "GFP-related fluorescent protein," which is exemplified by the various spectral variants and GFP mutants that have amino acid sequences that are substantially identical to A. Victoria GFP (SEQ ID NO: 2), to a "Discosoma-related fluorescent protein" or a "DsRed-related fluorescent related protein," which is exemplified by the various mutants that have amino acid sequences substantially identical to that of DsRed (SEQ ID NO: 12), and the like, for example, a Renilla-related fluorescent protein or a Phialidium-related fluorescent protein.

The term "mutant" or "variant" also is used herein in reference to a fluorescent protein to refer to a fluorescent protein that contains a mutation with respect to a corresponding wild type fluorescent protein. In addition, reference is made herein the a "spectral variant" or "spectral mutant" of a fluorescent protein to indicate a mutant fluorescent protein that has a different fluorescence characteristic with respect to the corresponding wild type fluorescent protein. For example, CFP, YFP, ECFP (SEQ ID NO: 6), EYFP-V68L/Q69K (SEQ ID NO: 10), and the like are GFP spectral variants.

Aequorea GFP-related fluorescent proteins include, for example, wild type (native) Aequorea victoria GFP (Prasher et al., supra, 1992; see, also, SEQ ID NO: 2), allelic variants of SEQ ID NO: 2, for example, a variant having a Q80R substitution (Chalfie et al., Science 263:802-805, 1994, which is incorporated herein by reference); and spectral variants of GFP such as CFP, YFP, and enhanced and otherwise modified forms thereof (U.S. Pat. Nos. 6,150,176; 6,124,128; 6,077,707; 6,066,476; 5,998,204; and 5,777,079, each of which is incorporated herein by reference), including GFP-related fluorescent proteins having one or more folding mutations, and fragments of the proteins that are fluorescent, for example, an *A. victoria* GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in *Aequorea* GFP-related fluorescent proteins improve the ability of the fluorescent proteins to fold at higher temperatures, and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO: 2, include the substitutions F64L, V68L, S72A, T44A, F99S, Y145F, N146I, M153T, M153A, V163A, I167T, S175G, S205T, and N212K.

The term "loop domain" refers to an amino acid sequence of an *Aequorea*-related fluorescent protein that connects the amino acids involved in the secondary structure of the eleven strands of the β-barrel or the central I-helix (residues 56-72). The term "fluorescent protein moiety," when used in reference to a fluorescent protein, refers to a portion of the amino acid sequence of the fluorescent protein that, when the amino acid sequence of the fluorescent protein substrate is optimally aligned with the amino acid sequence of a naturally occurring fluorescent protein, lies between the amino terminal and carboxy terminal amino acids, inclusive, of the amino acid sequence of the naturally occurring fluorescent protein, and comprises a chromophore, which fluoresces upon exposure to an appropriate wavelength of light.

Fluorescent proteins fused to target proteins can be prepared using recombinant DNA methods, and used as markers to identify the location and amount of the target protein produced. Accordingly, the present invention provides fusion proteins comprising a non-oligomerizing fluorescent protein moiety and a polypeptide of interest. The polypeptide of interest can be of any length, for example, about 15 amino acid residues, about 50 residues, about 150 residues, or up to about 1000 amino acid residues or more, provided that the fluorescent protein component of the fusion protein can fluoresce or can be induced to fluoresce when exposed to electromagnetic radiation of the appropriate wavelength. The polypeptide of interest can be, for example, a peptide tag such as a polyhistidine sequence, a c-myc epitope, a FLAG epitope, and the like; can be an enzyme, which can be used to effect a function in a cell expressing a fusion protein comprising the enzyme or to identify a cell containing the fusion protein; can be a protein to be examined for an ability to interact with one or more other proteins in a cell, or any other protein as disclosed herein or otherwise desired.

As disclosed herein, the *Discosoma* (coral) red fluorescent protein, DsRed, can be used as a complement to or alternative for a GFP or spectral variant thereof. Amino acid residues of DsRed that correspond to those of GFP have been identified, and mutations of selected amino acid residues, based on knowledge of the corresponding structures, has allowed the identification of DsRed mutants having different fluorescent properties as compared to wild type DsRed (see Example 2). In addition, DsRed is shown to have a propensity to oligomerize, similar to that dimerization that occurs for GFPs. As such, mutations can be made in DsRed and the identified mutants that correspond to those introduced into GFP that reduce or eliminate dimerization of GFPs (Examples 1 and 3). Furthermore, X-ray crystallography of DsRed and computer processing can be used to confirm that the optimal amino acid residues have been selected for mutation to reduce or eliminate oligomerization, similar to the model of the crystal structure of *Aequorea* GFP that was prepared (see U.S. Pat. No. 6,124,128). As further disclosed herein, non-oligomerizing tandem DsRed fluorescent proteins can be constructed, and the strategy used to design the tandem DsRed proteins can be applied to other fluorescent proteins (see Example 4).

Fluorescent characteristics of *Aequorea* GFP-related fluorescent proteins depend, in part, on the electronic environment of the chromophore. In general, amino acids that are within about 0.5 nm of the chromophore influence the electronic environment of the chromophore. Therefore, substitution of such amino acids can produce fluorescent proteins with altered fluorescent characteristics. In the excited state, electron density tends to shift from the phenolate towards the carbonyl end of the chromophore. Therefore, placement of increasing positive charge near the carbonyl end of the chromophore tends to decrease the energy of the excited state and cause a red-shift in the absorbance and emission wavelength maximum of the protein. Decreasing a positive charge near the carbonyl end of the chromophore tends to have the opposite effect, causing a blue-shift in the protein's wavelengths. Similarly, mutations have been introduced into DsRed to produce mutants having altered fluorescence characteristics (see Example 2).

Amino acids with charged (ionized D, E, K, and R), dipolar (H, N, Q, S, T, and uncharged D, E and K), and polarizable side groups (e.g., C, F, H, M, W and Y) are useful for altering the ability of fluorescent proteins to oligomerize, especially when they substitute an amino acid with an uncharged, nonpolar or non-polarizable side chain (see Examples 1 and 3). As disclosed herein, substitution of hydrophobic residues that were predicted to be involved in self-association of GFP with positively-charged residues reduced or eliminated dimerization. However, other non-conservative amino acid substitutions also can be introduced similarly or at neighboring positions in the interacting regions of the proteins, thus disrupting the localized structure of the protein, provided the substitutions do not undesirably affect the fluorescent properties of the proteins. Accordingly, the present invention provides non-oligomerizing fluorescent proteins.

A fusion protein, which includes a non-oligomerizing fluorescent protein, for example, a non-oligomerizing tandem fluorescent protein, operatively linked to one or more polypeptides of interest also is provided. The polypeptides of the fusion protein can be linked through peptide bonds, or the non-oligomerizing fluorescent protein can be linked to the polypeptide of interest through a linker molecule. In one embodiment, the fusion protein is expressed from a recombinant nucleic acid molecule containing a polynucleotide encoding a non-oligomerizing fluorescent protein operatively linked to one or more polynucleotides encoding one or more polypeptides of interest.

A polypeptide of interest can be any polypeptide, including, for example, a peptide tag such as a polyhistidine peptide, or a cellular polypeptide such as an enzyme, a G-protein, a growth factor receptor, or a transcription factor; and can be one of two or more proteins that can associate to form a complex. In one embodiment, the fusion protein is a tandem non-oligomerizing fluorescent protein construct, which includes a donor non-oligomerizing fluorescent protein, an acceptor non-oligomerizing fluorescent protein, and a peptide linker moiety coupling said donor and said acceptor, wherein cyclized amino acids of the donor emit light characteristic of said donor, and wherein the donor and the acceptor exhibit fluorescence resonance energy transfer when the donor is excited, and the linker moiety does not substantially emit light to excite the donor. As such, a fusion protein of the invention can include two or more operatively linked non-oligomerizing fluorescent proteins, which can be linked directly or indirectly, and can further comprise one or more polypeptides of interest.

A tandem non-oligomerizing fluorescent protein includes a donor, comprising a first fluorescent protein, an acceptor, comprising a second fluorescent protein, and a peptide linker moiety operatively linking the donor and the acceptor. In such a tandem non-oligomerizing fluorescent protein, the first fluorescent protein and second fluorescent protein are different, and at least the first fluorescent protein or the second fluorescent protein is a non-oligomerizing tandem fluorescent protein of the invention. In addition, the cyclized amino acids of the donor emit light characteristic of the donor, and the donor and the acceptor exhibit fluorescence resonance energy transfer when the donor is excited, and the linker moiety does not substantially emit light to excite the acceptor.

It should be recognized the reference to a "first" fluorescent protein or a "second" fluorescent protein or the like is used only to conveniently refer to a particular protein, but is not intended to indicate any order or importance of the protein. As such, where reference is made, for example, to a first non-oligomerizing tandem fluorescent protein and a second non-oligomerizing fluorescent protein, it will be recognized that either of the first or second fluorescent proteins can be the non-oligomerizing tandem fluorescent protein or can be the non-oligomerizing fluorescent protein.

In one embodiment, each of the first fluorescent protein and the second fluorescent protein is a non-oligomerizing tandem fluorescent protein in a tandem non-oligomerizing fluorescent protein of the invention. For example, the non-oligomerizing tandem fluorescent protein can comprise two or more *Discosoma* RFPs or a fluorescent protein related to a *Discosoma* RFP, such as a DsRed protein having an amino acid sequence as set forth in SEQ ID NO: 12 or a mutant DsRed protein such as SEQ ID NO:12 containing an I125R mutation. In another embodiment, the first fluorescent protein is a non-oligomerizing tandem fluorescent protein, and the second fluorescent protein is a non-oligomerizing fluorescent protein. The non-oligomerizing fluorescent protein can contain a mutation of an amino acid residue corresponding to A206, L221, F223, or a combination thereof of SEQ ID NO:2, for example, a mutation corresponding to S65G/S72A/T203Y/H231L in SEQ ID NO:2; a mutation corresponding to The present invention also provides a polynucleotide encoding a non-oligomerizing fluorescent protein, which can be a non-oligomerizing tandem fluorescent protein, as well as to a vector containing such a polynucleotide, and a host cell containing a polynucleotide or vector. Also provided is a recombinant nucleic acid molecule, which includes at least one polynucleotide encoding a non-oligomerizing fluorescent protein operatively linked to one or more other polynucleotides. The one or more other polynucleotides can be, for example, a transcription regulatory element such as a promoter or polyadenylation signal sequence, or a translation regulatory element such as a ribosome binding site. Such a recombinant nucleic acid molecule can be contained in a vector, which can be an expression vector, and the nucleic acid molecule or the vector can be contained in a host cell.

The vector generally contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther*. 1:51-64, 1994; Flotte, *J. Bioenerg. Biomemb*. 25:37-42, 1993; Kirshenbaum et al., *J. Clin. Invest*. 92:381-387, 1993; each of which is incorporated herein by reference).

A vector for containing a polynucleotide encoding a non-oligomerizing fluorescent protein can be a cloning vector or an expression vector, and can be a plasmid vector, viral vector, and the like. Generally, the vector contains a selectable marker independent of that encoded by a polynucleotide of the invention, and further can contain transcription or translation regulatory elements, including a promoter sequence, which can provide tissue specific expression of a polynucleotide operatively linked thereto, which can, but need not, be the polynucleotide encoding the non-oligomerizing fluorescent protein, for example, a non-oligomerizing tandem fluorescent protein, thus providing a means to select a particular cell type from among a mixed population of cells containing the introduced vector and recombinant nucleic acid molecule contained therein.

Where the vector is a viral vector, it can be selected based on its ability to infect one or few specific cell types with relatively high efficiency. For example, the viral vector also can be derived from a virus that infects particular cells of an organism of interest, for example, vertebrate host cells such as mammalian host cells. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med*. 334:1185-1187 (1996), each of which is incorporated herein by reference).

Recombinant production of a non-oligomerizing fluorescent protein, which can be a component of a fusion protein, involves expressing a polypeptide encoded by a polynucleotide. A polynucleotide encoding the non-oligomerizing fluorescent protein is a useful starting materials. Polynucleotides encoding fluorescent protein are disclosed herein or otherwise known in the art, and can be obtained using routine methods, then can be modified such that the encoded fluorescent protein lacks a propensity to oligomerize. For example, a polynucleotide encoding a GFP can be isolated by PCR of cDNA from *A. victoria* using primers based on the DNA sequence of *Aequorea* GFP (SEQ ID NO: 2). PCR methods are well known and routine in the art (see, for example, U.S. Pat. No. 4,683,195; Mullis et al., *Cold Spring Harbor Symp. Quant. Biol.* 51:263, 1987; Erlich, ed., "PCR Technology" (Stockton Press, NY, 1989)). A non-oligomerizing form of the fluorescent protein then can be made by site-specific mutagenesis of the polynucleotide encoding the fluorescent protein, or by random mutagenesis caused by increasing the error rate of PCR of the original polynucleotide with 0.1 mM $MnCl_2$ and unbalanced nucleotide concentrations (Example, 1; see, also, U.S. Pat. No. 6,066,476). Similarly, a non-oligomerizing tandem fluorescent protein can be expressed from a polynucleotide prepared by PCR using primers that can encode, for example, a peptide linker, which operatively links a first monomer and at least a second monomer of a fluorescent protein (see Example 4).

The construction of expression vectors and the expression of a polynucleotide in transfected cells involves the use of molecular cloning techniques also well known in the art (see Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Expression vectors contain expression control sequences operatively linked to a polynucleotide sequence of interest, for example, that encoding a non-oligomerizing fluorescent protein, as indicated above. The expression vector can be adapted for function in prokaryotes or eukaryotes by inclusion of appropriate promoters, replication sequences, markers, and the like. An expression vector can be transfected into a recombinant host cell for expression of a non-oligomerizing fluorescent protein, and host cells can be selected, for example, for high levels of expression in order to obtain a large amount of isolated protein. A host cell can be maintained in cell culture, or can be a cell in vivo in an organism. A non-oligomerizing fluorescent protein can be produced by expression from a polynucleotide encoding the protein in a host cell such as *E. coli*. *Aequorea* GFP-related fluorescent proteins, for example, are best expressed by cells cultured between about 15° C. and 30° C., although higher temperatures such as 37° C. can be used. After synthesis, the fluorescent proteins are stable at higher temperatures and can be used in assays at such temperatures.

An expressed non-oligomerizing fluorescent protein, which can be a non-oligomerizing tandem fluorescent protein and can be operatively linked to a first polypeptide of interest, further can be linked to a second polypeptide of interest, for example, a peptide tag, which can be used to facilitate isolation of the non-oligomerizing fluorescent protein, including any other polypeptides linked thereto. For example, a polyhistidine tag containing, for example, six histidine residues, can be incorporated at the N-terminus or C-terminus of the non-oligomerizing fluorescent protein, which then can be isolated in a single step using nickel-chelate chromatography (see Example, 1). Additional peptide tags, including a c-myc peptide, a FLAG epitope, or any ligand (or cognate receptor), including any peptide epitope (or antibody, or antigen binding fragment thereof, that specifically binds the epitope are well known in the art and similarly can be used. (see, for example, Hopp et al., *Biotechnology* 6:1204 (1988); U.S. Pat. No. 5,011,912, each of which is incorporated herein by reference).

Kits also are provided to facilitate and, where desired, standardize the compositions of the invention and the uses thereof. A kit can contain one or more compositions of the invention, for example, one or a plurality of non-oligomerizing fluorescent proteins, which can be a portion of a fusion protein, or one or a plurality of polynucleotides that encode the polypeptides. The non-oligomerizing fluorescent protein can be a mutated fluorescent protein having a reduced propensity to oligomerize or can be a non-oligomerizing tandem fluorescent protein and, where the kit comprises a plurality of non-oligomerizing fluorescent proteins, the plurality can be a plurality of the mutated non-oligomerizing fluorescent proteins, or of the non-oligomerizing tandem fluorescent proteins, or a combination thereof.

A kit of the invention also can contain one or a plurality of recombinant nucleic acid molecules, which encode, in part, non-oligomerizing fluorescent proteins, which can be the same or different, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions of the invention that are contained in the kit.

Such kits can be particularly useful where they provide a plurality of different non-oligomerizing fluorescent proteins because the artisan can conveniently select one or more proteins having the fluorescent properties desired for a particular application. Similarly, a kit containing a plurality of polynucleotides encoding different non-oligomerizing fluorescent proteins provides numerous advantages. For example, the polynucleotides can be engineered to contain convenient restriction endonuclease or recombinase recognition sites, thus facilitating operative linkage of the polynucleotide to a regulatory element or to a polynucleotide encoding a polypeptide of interest or, if desired, for operatively linking two or more the polynucleotides encoding the non-oligomerizing fluorescent proteins to each other.

A non-oligomerizing fluorescent protein of the invention is useful in any method that employs a fluorescent proteins. Thus, the non-oligomerizing fluorescent proteins, including the non-oligomerizing tandem fluorescent proteins, are useful as fluorescent markers in the many ways fluorescent markers already are used, including, for example, coupling non-oligomerizing fluorescent proteins to antibodies, polynucleotides or other receptors for use in detection assays such as immunoassays or hybridization assays, or to track the movement of proteins in cells. For intracellular tracking studies, a first (or other) polynucleotide encoding the non-oligomerizing fluorescent protein is fused to a second (or other) polynucleotide encoding a protein of interest and the construct, if desired, can be inserted into an expression vector. Upon expression inside the cell, the protein of interest can be localized based on fluorescence, without concern that localization of the protein is an artifact caused by oligomerization of the fluorescent protein component of the fusion protein. In one embodiment of this method, two proteins of interest independently are fused with two non-oligomerizing fluorescent proteins that have different fluorescent characteristics.

The non-oligomerizing fluorescent proteins of this invention are useful in systems to detect induction of transcription. For example, a nucleotide sequence encoding a non-oligomerizing tandem fluorescent protein can be fused to a promoter or other expression control sequence of interest, which can be contained in an expression vector, the construct can be transfected into a cell, and induction of the promoter (or other regulatory element) can be measured by detecting the presence or amount of fluorescence, thereby allowing a means to observe the responsiveness of a signaling pathway from receptor to promoter.

A non-oligomerizing fluorescent protein of the invention also is useful in applications involving FRET, which can detect events as a function of the movement of fluorescent donors and acceptors towards or away from each other. One or both of the donor/acceptor pair can be a non-oligomerizing fluorescent protein, for example, a donor GFP having a T203I mutation and an acceptor GFP having the mutation T203X, wherein X is an aromatic amino acid, for example, T203Y, T203W, or T203H (see U.S. Pat. Nos. 6,124,128 and 6,066,476). Another useful donor/acceptor pair includes a donor having the mutations S72A, K79R, Y145F, M153A and T203I (with a excitation peak of 395 nm and an emission peak of 511 nm) and an acceptor having the mutations S65G, S72A, K79R, and T203Y. Such a donor/acceptor pair provides a wide separation between the excitation and emission peaks of the donor, and provides good overlap between the donor emission spectrum and the acceptor excitation spectrum. Other non-oligomerizing red fluorescent proteins or red-shifted mutants as disclosed herein can also be used as the acceptor in such a pair.

FRET can be used to detect cleavage of a substrate having the donor and acceptor coupled to the substrate on opposite sides of the cleavage site. Upon cleavage of the substrate, the donor/acceptor pair physically separate, eliminating FRET. Such an assay can be performed, for example, by contacting the substrate with a sample, and determining a qualitative or quantitative change in FRET (see, for example, U.S. Pat. No. 5,741,657, which is incorporated herein by reference). A non-oligomerizing fluorescent protein donor/acceptor pair also can be part of a fusion protein coupled by a peptide having a proteolytic cleavage site (see, for example, U.S. Pat. No. 5,981,200, which is incorporated herein by reference). FRET also can be used to detect changes in potential across a membrane. For example, a donor and acceptor can be placed on opposite sides of a membrane such that one translates across the membrane in response to a voltage change, thereby producing a measurable FRET (see, for example, U.S. Pat. No. 5,661,035, which is incorporated herein by reference).

A non-oligomerizing fluorescent protein of the invention is useful for making a fluorescent substrate for a protein kinase. Such a substrate incorporates an amino acid sequence recognizable by a protein kinases and, upon phosphorylation, the non-oligomerizing fluorescent protein undergoes a change in a fluorescent property. Such substrates are useful for detecting and measuring protein kinase activity in a sample of a cell, upon transfection and expression of the substrate. Preferably, the kinase recognition site is placed within about 20 amino acids of a terminus of the non-oligomerizing fluorescent protein, or in a loop domain of the protein (see U.S. Ser. No. 08/680,877, filed Jul. 16, 1996, which is incorporated herein by reference). Similarly, a protease recognition site also can be introduced into a loop domain such that, upon cleavage, the fluorescent property changes in a measurable fashion.

Fluorescence in a sample generally is measured using a fluorimeter, wherein excitation radiation from an excitation source having a first wavelength, passes through excitation optics, which cause the excitation radiation to excite the sample. In response, a non-oligomerizing fluorescent protein in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. These and other methods of performing assays on fluorescent materials are well known in the art (see, for example, Lakowicz, "Principles of Fluorescence Spectroscopy" (Plenum Press 1983); Herman, "Resonance energy transfer microscopy" In "Fluorescence Microscopy of Living Cells in Culture" Part B, *Meth. Cell Biol*. 30:219-243 (ed. Taylor and Wang; Academic Press 1989); Turro, "Modem Molecular Photochemistry" (Benjamin/Cummings Publ. Co., Inc. 1978), pp. 296-361, each of which is incorporated herein by reference).

Accordingly, the present invention provides a method for identifying the presence of a molecule in a sample. Such a method can be performed, for example, by linking a non-oligomerizing fluorescent protein of the invention to the molecule, and detecting fluorescence due to the non-oligomerizing fluorescent protein in a sample suspected of containing the molecule. The molecule to be detected can be a polypeptide, a polynucleotide, or any other molecule, including, for example, an antibody, an enzyme, or a receptor, and the non-oligomerizing fluorescent protein can be a non-oligomerizing tandem fluorescent protein.

The sample to be examined can be any sample, including a biological sample, an environmental sample, or any other sample for which it is desired to determine whether a particular molecule is present therein. Preferably, the sample includes a cell or an extract thereof. The cell can be obtained from a vertebrate, including a mammal such as a human, or from an invertebrate, and can be a cell from a plant or an animal. The cell can be obtained from a culture of such cells, for example, a cell line, or can be isolated from an organism. As such, the cell can be contained in a tissue sample, which can be obtained from an organism by any means commonly used to obtain a tissue sample, for example, by biopsy of a human. Where the method is performed using an intact living cell or a freshly isolated tissue or organ sample, the presence of a molecule of interest in living cells can be identified, thus providing a means to determine, for example, the intracellular compartmentalization of the molecule. The use of the non-oligomerizing fluorescent proteins of the invention for such a purpose provides a substantial advantage in that the likelihood of aberrant identification or localization due to oligomerization the fluorescent protein is greatly minimized.

A non-oligomerizing fluorescent protein can be linked to the molecule directly or indirectly, using any linkage that is stable under the conditions to which the protein-molecule complex is to be exposed. Thus, the fluorescent protein and molecule can be linked via a chemical reaction between reactive groups present on the protein and molecule, or the linkage can be mediated by linker moiety, which contains reactive groups specific for the fluorescent protein and the molecule. It will be recognized that the appropriate conditions for linking the non-oligomerizing fluorescent protein and the molecule are selected depending, for example, on the chemical nature of the molecule and the type of linkage desired. Where the molecule of interest is a polypeptide, a convenient means for linking a non-oligomerizing fluorescent protein and the molecule is by expressing them as a fusion protein from a recombinant nucleic acid molecule, which comprises a polynucleotide encoding, for example, a non-oligomerizing tandem fluorescent protein operatively linked to a polynucleotide encoding the polypeptide molecule.

A method of identifying an agent or condition that regulates the activity of an expression control sequence also is provided. Such a method can be performed, for example, by exposing a recombinant nucleic acid molecule, which includes a polynucleotide encoding a non-oligomerizing fluorescent protein operatively linked to an expression control sequence, to an agent or condition suspected of being able to regulate expression of a polynucleotide from the expression control sequence, and detecting fluorescence of the non-oligomerizing fluorescent protein due to such exposure. Such a method is useful, for example, for identifying chemical or biological agents, including cellular proteins, that can regulate expression from the expression control sequence, including cellular factors involved in the tissue specific expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

The non-oligomerizing fluorescent proteins of the invention also are useful in a method of identifying a specific interaction of a first molecule and a second molecule. Such a method can be performed, for example, by contacting the first molecule, which is linked to a donor first non-oligomerizing fluorescent protein, and the second molecule, which is linked to an acceptor second non-oligomerizing fluorescent protein, under conditions that allow a specific interaction of the first molecule and second molecule; exciting the donor; and detecting fluorescence resonance energy transfer from the donor to the acceptor, thereby identifying a specific interaction of the first molecule and the second molecule. The conditions for such an interaction can be any conditions under which it is expected or suspected that the molecules can specifically interact. In particular, where the molecules to be examined are cellular molecules, the conditions generally are physiological conditions. As such, the method can be performed in vitro using conditions of buffer, pH, ionic strength, and the like, that mimic physiological conditions, or the method can be performed in a cell or using a cell extract.

The first and second molecules can be cellular proteins that are being investigated to determine whether the proteins specifically interact, or to confirm such an interaction. Such first and second cellular proteins can be the same, where they are being examined, for example, for an ability to oligomerize, or they can be different where the proteins are being examined as specific binding partners involved, for example, in an intracellular pathway. The first and second molecules also can be a polynucleotide and a polypeptide, for example, a polynucleotide known or to be examined for transcription regulatory element activity and a polypeptide known or being tested for transcription factor activity. For example, the first molecule can comprise a plurality of nucleotide sequences, which can be random or can be variants of a known sequence, that are to be tested for transcription regulatory element activity, and the second molecule can be a transcription factor, such a method being useful for identifying novel transcription regulatory elements having desirable activities.

The present invention also provides a method for determining whether a sample contains an enzyme. Such a method can be performed, for example, by contacting a sample with a tandem non-oligomerizing fluorescent protein of the invention; exciting the donor, and determining a fluorescence property in the sample, wherein the presence of an enzyme in the sample results in a change in the degree of fluorescence resonance energy transfer. Similarly, the present invention relates to a method for determining the activity of an enzyme in a cell. Such a method can be performed, for example, providing a cell that expresses a tandem non-oligomerizing fluorescent protein construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

Also provided is a method for determining the pH of a sample. Such a method can be performed, for example, by contacting the sample with a first non-oligomerizing fluorescent protein, which can be a non-oligomerizing tandem fluorescent protein, wherein the emission intensity of the first non-oligomerizing fluorescent protein changes as pH varies between pH 5 and pH 10; exciting the indicator; and determining the intensity of light emitted by the first non-oligomerizing fluorescent protein at a first wavelength, wherein the emission intensity of the first non-oligomerizing fluorescent protein indicates the pH of the sample. The first non-oligomerizing fluorescent protein useful in this method, or in any method of the invention, can comprise two DsRed monomers as set forth in SEQ ID NO:12, or a mutant thereof such as an I125R mutant, operatively linked, for example, by a peptide having an amino acid sequence of SEQ ID NO:26; or can have an amino acid sequence of SEQ ID NO: 2, or a sequence substantially identical thereto, for example, having the mutations S65G/S72A/T203Y/H231L with respect to SEQ ID NO:2, or the mutations S65G/V68L/Q69K/S72A/T203Y/H231L with respect to SEQ ID NO:2; or the mutations K26R/F64L/S65T/Y66W/N146I/M153T/V163A/N164H/H231L with respect to SEQ ID NO:2; or any of the above mutated non-oligomerizing fluorescent protein further having a mutation corresponding to H148G or H148Q with respect to SEQ ID NO: 2. It will be recognized that such non-oligomerizing fluorescent proteins similarly are useful, either alone or in combination, for the variously disclosed methods of the invention.

The sample used in a method for determining the pH of a sample can be any sample, including, for example, a biological tissue sample, or a cell or a fraction thereof. In addition, the method can further include contacting the sample with a second non-oligomerizing fluorescent protein, wherein the emission intensity of the second non-oligomerizing fluorescent protein changes as pH varies from 5 to 10, and wherein the second non-oligomerizing fluorescent protein emits at a second wavelength that is distinct from the first wavelength; exciting the second non-oligomerizing fluorescent protein; determining the intensity of light emitted by the second non-oligomerizing fluorescent protein at the second wavelength; and comparing the fluorescence at the second wavelength to the fluorescence at the first wavelength. The first (or second) non-oligomerizing fluorescent protein can include a targeting sequence, for example, a cell compartmentalization domain such a domain that targets the non-oligomerizing fluorescent protein in a cell to the cytosol, the endoplasmic reticulum, the mitochondrial matrix, the chloroplast lumen, the medial trans-Golgi cisternae, a lumen of a lysosome, or a lumen of an endosome. For example, the cell compartmentalization domain can include amino acid residues 1 to 81 of human type II membrane-anchored protein galactosyltransferase, or amino acid residues 1 to 12 of the presequence of subunit IV of cytochrome c oxidase.

The following examples are intended to illustrate, but not limit, the present invention.

EXAMPLE 1

Preparation and Characterization of Non-oligomerizing Fluorescent Proteins

This example demonstrates that mutations can be introduced into GFP spectral variants that reduce or eliminate the ability of the proteins to oligomerize.

ECFP (SEQ ID NO: 6) and EYFP-V68L/Q69K (SEQ ID NO: 10) at the dimer interface were subcloned into the bacterial expression vector pRSET$_B$ (Invitrogen Corp., La Jolla Calif.), creating an N-terminal His$_6$ tag on the of ECFP (SEQ ID NO: 6) and EYFP-V68L/Q69K (SEQ ID NO: 10), which allowed purification of the bacterially expressed proteins on a nickel-agarose (Qiagen) affinity column. All dimer-related mutations in the cDNAs were created by site-directed mutagenesis using the QuickChange mutagenesis kit (Stratagene), then expressed and purified in the same manner. All cDNAs were sequenced to ensure that only the desired mutations existed.

EYFP-V68L/Q69K (SEQ ID NO: 10) was mutagenized using the QuickChange kit (Stratagene). The overlapping mutagenic primers were designated "top" for the 5' primer and "bottom" for the 3' primer and are designated according to the particular mutation introduced (see Table 1). All primers had a melting temperature greater than 70° C. The mutations were made as close to the center of the primers as possible and all primers were purified by polyacrylamide gel electrophoresis. The primers are shown in a 5' to 3' orientation, with mutagenized codons underlined (Table 1).

TABLE 1

```
A206K   CAG TCC AAG CTG AGC AAA GAC  (SEQ ID NO: 13)
top     CCC AAC GAG AAG CGC GAT CAC A206K   GTG ATC GCG CTT CTC GTT GGG  (SEQ ID NO: 14)
bottom  GTC TTT GCT CAG CTT GGA CTG L221K   CAC ATG GTC CTG AAG GAG TTC  (SEQ ID NO: 15)
top     GTG ACC GCC GCC GGG L221K   CCC GGC GGC GGT CAC GAA CTC  (SEQ ID NO: 16)
bottom  CTT CAG GAC CAT GTG F223R   CAC ATG GTC CTG CTG GAG CGC  (SEQ ID NO: 17)
top     GTG ACC GCC GCC GGG F223R   CCC GGC GGC GGT CAC GCG CTC  (SEQ ID NO: 18)
bottom  CAG CAG GAC CAT GTG L221K/  CAC ATC GTC CTG AAG GAG CGC  (SEQ ID NO: 19)
F223R   GTG ACC GCC GCC GGG
top L221K/  CCC GGC GGC GGT CAC GCG CTC  (SEQ ID NO: 20)
F223R   CTT CAG GAC CAT GTG
bot.
```

For protein expression, plasmids containing cDNAs for the various EYFP-V68L/Q69K (SEQ ID NO: 10) mutants were transformed into *E. coli* strain JM109 and grown to an OD$_{600}$ of 0.6 in LB containing 100 µg/ml ampicillin at which time they were induced with 1 mM isopropyl β-D-thiogalactoside. The bacteria were allowed to express the protein at room temperature for 6 to 12 hr, then overnight at 4° C., then were pelleted by centrifugation, resuspended in phosphate buffered saline (pH 7.4), and lysed in a French press. Bacterial lysates were cleared by centrifugation at 30,000×g for 30 min. The proteins in the cleared lysates were affinity-purified on Ni-NTA-agarose (Qiagen).

All GFPs used in these experiments were 238 amino acids in length. Subcloning the cDNAs encoding the GFPs into pRSET$_B$ resulted in the fusion of an additional 33 amino acids to the N-terminus of the GFPs. The sequence of this tag is MRGSHHHHHHGMASMTGGQQMGRDLYD-DDDKDP (SEQ ID NO: 21). Thus, the total length of the EYFP-V68L/Q69K (SEQ ID NO: 10) mutants expressed from this cDNA was 271 amino acids. The His$_6$ tag was removed using EKMax (Invitrogen) to determine if the associative properties measured for the GFPs were affected by the presence of the N-terminal His$_6$-tag. A dilution series of the enzyme and His$_6$-tagged GFP was made to determine the conditions necessary for complete removal of the His$_6$-tag. The purity of all expressed and purified proteins was analyzed by SDS-PAGE. In all cases, the expressed proteins were very pure, with no significant detectable contaminating proteins, and all were of the proper molecular weight. In addition, removal of the His$_6$ tag was very efficient, as determined by the presence of a single band migrating at the lower molecular weight than the His$_6$-EYFP-V68L/Q69K.

Spectrophotometric analysis of the purified proteins determined that there was no significant change in either the extinction coefficient as measured by chromophore denaturation (Ward, supra, 1998) or quantum yield (the standard used for EYFP-V68L/Q69K and the mutants derived therefrom was fluorescein) of these proteins with respect to EYFP-V68L/Q69K (SEQ ID NO: 10; "wtEYFP"; Table 2). Fluorescence spectra were taken with a Fluorolog spectrofluorimeter. Absorbance spectra of proteins were taken with a Cary UV-Vis spectrophotometer. Extinction coefficients were determined by the denatured chromophore method (Ward, supra, 1998).

TABLE 2

| Protein | Quantum Yield | Extinction Coefficient |
|---|---|---|
| WtEYFP | 0.71* | 62,000* |
| His$_6$ wtEYFP | 0.67 | 67,410 |
| His$_6$ wtEYFP L221K | 0.67 | 64,286 |
| His$_6$ wtEYFP F223R | 0.53 | 65,393 |
| His$_6$ wtEYFP A206K | 0.62 | 79,183 |

*published data (Cubitt et al., 1997)

To determine the degree of homoaffinity of the dimers, wtEYFP and the dimer mutants derived therefrom were subjected to sedimentation equilibrium analytical ultracentrifugation. Purified, recombinant proteins were dialyzed extensively against phosphate buffered saline (pH 7.4), and 125 µl samples of protein at concentrations ranging from 50 µM to 700 µM were loaded into 6-channel centrifugation cells with EPON centerpieces. Samples were blanked against the corresponding dialysis buffer. Sedimentation equilibrium experiments were performed on a Beckman Optima XL-I analytical ultracentrifuge at 20° C. measuring radial absorbance at 514 nm. Each sample was examined at three or more of the following speeds: 8,000 rpm, 10,000 rpm, 14,000 rpm, and 20,000 rpm. Periodic absorbance measurements at each speed ensured that the samples had reached equilibrium at each speed.

The data were analyzed globally at all rotor speeds by nonlinear least-squares analysis using the software package (Origin) supplied by Beckman. The goodness of fit was evaluated on the basis of the magnitude and randomness of the residuals, expressed as the difference between the experimental data and the theoretical curve and also by checking each of the tit parameters for physical reasonability. The molecular weight and partial specific volume of each protein were determined using Sedenterp v 1.01, and the data were factored into the equation for the determination of homoaffinity (Table 3). In addition, dissociation constants ($K_d$) derived from the data generated by analytical ultracentrifugation are shown for some proteins (Table 4).

TABLE 3

| Mutant | Molecular Weight | Partial Specific Volume |
|---|---|---|
| wtEYFP | 26796.23 | 0.7332 |
| His$_6$ wtEYFP | 30534.26 | 0.7273 |
| His$_6$ EYFP A206K | 30593.37 | 0.7277 |
| EYFP L221K | 30551.29 | 0.7270 |
| His$_6$ EYFP L221K | 30549.27 | 0.7271 |
| His$_6$ EYFP F223R | 30543.27 | 0.7270 |
| His$_6$ EYFP L221K/F223R | 30560.30 | 0.7267 |

TABLE 4

| Protein | $K_d$(mM) |
|---|---|
| His$_6$ wtEYFP | 0.11 |
| His$_6$ wtEYFP L221K | 9.7 |
| His$_6$ wtEYFP F223R | 4.8 |
| His$_6$ wtEYFP A206K | 74 |
| His$_6$ wtEYFP L221K/F223R | 2.4 |

For experiments in living cells, ECFP (SEQ ID NO: 6; "wtECFP") and EYFP-V68L/Q69K (SEQ ID NO: 10; "wtEYFP") targeted to the plasma membrane (PM) were subcloned into the mammalian expression vector, pcDNA3 (Invitrogen Corp.) and mutagenized and sequenced as described above. Targeting of the GFP variants to the PM was accomplished by making either N-terminal or C-terminal fusions of the GFP variant to short peptides containing a consensus sequence for acylation and/or prenylation (post-translational lipid modifications). The cDNAs of the PM targeted GFP variants were transfected and expressed in either HeLa cells or MDCK cells, and the expression pattern and degree of association were determined using fluorescent microscopy. FRET efficiency was measured to determine the degree of interaction of the PM-ECFP and PM-EYFP-V68L/Q69K. Analysis of the interactions by the FRET donor-dequench method (Miyawaki and Tsien, supra, 2000) demonstrated that the wtECFP and wtEYFP interacted in a manner that was dependent upon the association of the wtECFP and wtEYFP, and that this interaction was effectively eliminated by changing the amino acids in the hydrophobic interface to any one or a combination of the mutations A206K, L221K and F223R.

These results demonstrate that the solution oligomeric state of *Aequorea* GFP and its spectral variants, and dimer mutants derived therefrom, were accurately determined by analytical ultracentrifugation. The ECFP (SEQ ID NO: 6) and EYFP-V68L/Q69K (SEQ ID NO: 10) GFP spectral variants formed homodimers with a fairly high affinity of about 113 µM. By using site directed mutagenesis, the amino acid composition was altered so as to effectively eliminate dimerization and the cell biological problems associated with it. Thus, the modified fluorescent proteins provide a means to use FRET to measure the associative properties of host proteins fused to the modified CFP or YFP. The ambiguity and potential for false positive FRET results associated with ECFP (SEQ ID NO: 6) and EYFP-V68L/Q69K (SEQ ID NO: 10) dimerization have been effectively eliminated, as has the possibility of misidentification of the subcellular distribution or localization of a host protein due to dimerization of GFPs.

The *Renilla* GFP and the *Discosoma* red fluorescent protein (see Example 2) are obligate oligomers in solution. Because it was generally believed that *Aequorea* GFP could also dimerize in solution, and because GFP crystallizes as a dimer, the present investigation was designed to characterize the oligomeric state of GFP. The crystallographic interface between the two monomers included many hydrophilic contacts as well as several hydrophobic contacts (Yang et al., supra, 1996). It was not immediately clear, however, to what degree each type of interaction contributed to the formation of the dimer in solution.

As disclosed herein, the extent of GFP self-association was examined using sedimentation equilibrium, analytical ultracentrifugation, which is very useful for determining the oligomeric behavior of molecules both similar (self associating homomeric complexes) and dissimilar (heteromeric complexes; see Laue and Stafford, *Ann. Rev. Biophys. Biomol. Struct.* 28:75-100, 1999). In contrast to X-ray crystallography, the experimental conditions used in the analytical ultracentrifugation experiments closely approximated cellular physiological conditions. Monomer contact sites identified by X-ray crystallography within a multimeric complex are not necessarily the same as those in solution. Also in contrast to analytical ultracentrifugation, X-ray crystallography alone cannot provide definitive information about the affinity of the complex. The results of this investigation demonstrate that replacement of the hydrophobic residues A206, L221 and F223 with residues containing positively charged side chains (A206K, L221K and F223R) eliminated dimerization as determined by analytical ultracentrifugation in vitro and by analysis of the concentration dependence of FRET in intact cells.

EXAMPLE 2

Characterization of the Coral Red Fluorescent Protein, DsRed and Mutants Thereof This example describes the biochemical and biological characterization of DsRed and DsRed mutants.

The coding sequence for DsRed was amplified from pDsRed-N1 (Clontech Laboratories) with PCR primers that added an N terminal Bam HI recognition site upstream of the initiator Met codon and a C terminal Eco RI site downstream of the STOP codon. After restriction digestion, the PCR product was cloned between the Bam HI and Eco RI sites of pRSET$_B$ (Invitrogen), and the resulting vector was amplified in DH5α bacteria. The resulting plasmid was used as a template for error-prone PCR (Heim and Tsien, *Curr. Biol.* 6:178-182, 1996, which is incorporated herein by reference) using primers that were immediately upstream and downstream of the DsRed coding sequence, theoretically allowing mutation of every coding base, including the initiator Met.

The mutagenized PCR fragment was digested with Eco RI and Bam HI and recloned into pRSET$_B$. Alternatively, the Quick-Change mutagenesis kit (Stratagene) was used to make directed mutations on the pRSET$_B$-DsRed plasmid.

In both random and directed mutagenesis studies, the mutagenized plasmid library was electroporated into JM109 bacteria, plated on LB plates containing ampicillin, and screened on a digital imaging device (Baird et al., *Proc. Natl. Acad. Sci., USA* 96:11242-11246, 1999, which is incorporated herein by reference). This device illuminated plates with light from a 150 Watt xenon arc lamp, filtered through bandpass excitation filters and directed onto the plates with two fiber optic bundles. Fluorescence emission from the plates was imaged through interference filters with a cooled CCD camera. Images taken at different wavelengths could be digitally ratioed using MetaMorph software (Universal Imaging) to allow identification of spectrally shifted mutants. Once selected, the mutant colonies were picked by hand into LB/Amp medium, after which the culture was used for protein preparation or for plasmid preparations. The DsRed mutant sequences were analyzed with dye-terminator dideoxy sequencing.

DsRed and its mutants were purified using the N-terminal polyhistidine tag (SEQ ID NO: 21; see Example 1) provided by the pRSET$_B$ expression vector (see Baird et al., supra, 1999). The proteins were microconcentrated and buffer exchanged into 10 mM Tris (pH 8.5) using a Microcon-30 (Amicon) for spectroscopic characterization. Alternatively, the protein was dialyzed against 10 mM Tris (pH 7.5) for oligomerization studies because microconcentration resulted in the production of large protein aggregates. To test for light sensitivity of protein maturation, the entire synthesis was repeated in the dark, with culture flasks wrapped in foil, and all purification was performed in a room that was dimly lit with red lights. There was no difference in protein yield or color when the protein was prepared in light or dark.

Numbering of amino acids conforms to the wild type sequence of drFP583 (DsRed; Matz et al., supra, 1999), in which residues 66-68, Gln-Tyr-Gly, are homologous to the chromophore-forming residues (65-67, Ser-Tyr-Gly) of GFP. The extra amino acid introduced by Clontech after the initiator Met was numbered "1a" and the residues of the N-terminal polyhistidine tag were numbered $^-$33 to $^-$1.

Fluorescence spectra were taken with a Fluorolog spectrofluorimeter. Absorbance spectra of proteins were taken with a Cary UV-Vis spectrophotometer. For quantum yield determination, the fluorescence of a solution of DsRed or DsRed K83M in phosphate buffered saline was compared to equally absorbing solutions of Rhodamine B and Rhodamine 101 in ethanol. Corrections were included in the quantum yield calculation for the refractive index difference between ethanol and water. For extinction coefficient determination, native protein absorbance was measured with the spectrophotometer, and protein concentration was measured by the BCA method (Pierce).

The pH sensitivity of DsRed was determined in a 96 well format by adding 100 µl of dilute DsRed in a weakly buffered solution to 100 µl of strongly buffered pH solutions in triplicate (total 200 µl per well) for pH 3 to pH 12. The fluorescence of each well was measured using a 525-555 nm bandpass excitation filter and a 575 nm long pass emission filter. After the 96 well fluorimeter measurements were taken, 100 µl of each pH buffered DsRed solution was analyzed on the spectrofluorimeter to observe pH-dependent spectral shape changes. For time-trials of DsRed maturation, a dilute solution of freshly synthesized and purified DsRed was made in 10 mM Tris (pH 8.5), and this solution was stored at room temperature in a stoppered cuvette (not airtight) and subjected to periodic spectral analysis. For mutant maturation data, fluorescence emission spectra (excitation at 475 nm or 558 nm) were taken directly after synthesis and purification, and then after more than 2 months storage at 4° C. or at room temperature.

Quantum yields for photodestruction were measured separately on a microscope stage or in a spectrofluorimeter. Microdroplets of aqueous DsRed solution were created under oil on a microscope slide and bleached with 1.2 W/cm$^2$ of light through a 525-555 nm bandpass filter. Fluorescence over time was monitored using the same filter and a 563-617 nm emission filter. For comparison, EGFP (containing mutations F64L, S65T; SEQ ID NO: 6) and EYFP-V68L/Q69K (also containing mutations S65G, S72A, T203Y; SEQ ID NO: 10) microdroplets were similarly bleached with 1.9 W/cm$^2$ at 460-490 nm while monitoring at 515-555 and 523-548 nm, respectively.

For the spectrofluorimeter bleaching experiment, a solution of DsRed was prepared in a rectangular microcuvette and overlaid with oil so that the entire 50 µl of protein solution resided in the 0.25 cm×0.2 cm×1 cm illumination volume. The protein solution was illuminated with 0.02 W/cm$^2$ light from the monochromator centered at 558 nm (5 nm bandwidth). Fluorescence over time was measured at 558 nm excitation (1.25 nm bandwidth) and 583 nm emission. Quantum yields ($\Phi$) for photobleaching were deduced from the equation $\Phi=(\epsilon \cdot I \cdot t_{90\%})^{-1}$, where $\epsilon$ is the extinction coefficient in cm$^2$mol$^{-1}$, I is the intensity of incident light in einsteins cm$^{-2}$s$^{-1}$ and $t_{90\%}$ is the time in seconds for the fluorophore to be 90% bleached (Adams et al., *J. Am. Chem. Soc.* 110:3312-3320, 1988, which is incorporated herein by reference).

Polyhistidine-tagged DsRed, DsRed K83M and wild type *Aequorea* GFP (SEQ ID NO: 2) were run on a 15% polyacrylamide gel without denaturation. To prevent denaturation, protein solutions (in 10 mM Tris HCl, pH 7.5) were mixed 1:1 with 2×SDS-PAGE sample buffer (containing 200 mM dithiothreitol) and loaded directly onto the gel without boiling. A broad range pre-stained molecular weight marker set (BioRad) was used as a size standard. The gel was then imaged on an Epson 1200 Perfection flatbed scanner.

Purified recombinant DsRed was dialyzed extensively against phosphate buffered saline (pH 7.4) or 10 mM Tris, 1 mM EDTA (pH 7.5). Sedimentation equilibrium experiments were performed on a Beckman Optima XL-I analytical ultracentrifuge at 20° C. measuring absorbance at 558 nm as a function of radius. 125 µl samples of DsRed at 3.57 µM (0.25 absorbance units) were loaded into 6 channel cells. The data were analyzed globally at 10,000, 14,000, and 20,000 rpm by nonlinear least-squares analysis using the Origin software package (Beckman). The goodness of fit was evaluated on the basis of the magnitude and randomness of the residuals, expressed as the difference between the experimental data and the theoretical curve and also by checking each of the fit parameters for physical reasonability.

FRET between immature green and mature red DsRed was examined in mammalian cells. DsRed in the vector pcDNA3 was transfected into HeLa cells using Lipofectin, and 24 hr later the cells were imaged on a fluorescence microscope. The fluorescences of the immature green species (excitation 465-495 nm, 505 nm dichroic, emission 523-548 nm) and of mature red protein (excitation 529-552 nm, 570 nm dichroic, emission 563-618 nm) were measured with a cooled CCD camera. These measurements were repeated after selective photobleaching of the red component by illumination with light from the xenon lamp, filtered only by the 570 nm dichroic, for cumulative durations of 3, 6, 12, 24, and 49 min. By the final time, about 95% of the initial red emission had disappeared, whereas the green emission was substantially enhanced.

Yeast two hybrid assays were also performed. The DsRed coding region was cloned in-frame downstream of the Gal4 activation domains (the "bait"; amino acid residues 768-881) and DNA binding domains (the "prey"; amino acid residues 1-147) in the pGAD GH and pGBT9 vectors, respectively (Clontech). These DsRed two hybrid plasmids were transformed into the HF7C strain of *S. cerevisiae*, which cannot synthesize histidine in the absence of interaction between the proteins fused to the Gal4 fragments. Yeast containing both DsRed-bait and DsRed-prey plasmids were streaked on medium lacking histidine and assayed for growth by visually inspecting the plates. Alternatively, the yeast were grown on filters placed on plates lacking tryptophan and leucine to select for the bait and prey plasmids. After overnight growth, the filters were removed from the plates, frozen in liquid nitrogen, thawed, and incubated in X-gal overnight at 30° C. and two days at 4° C. to test for β-galactosidase activity (assayed by blue color development). In both the β-galactosidase and histidine growth assays, negative controls consisted of yeast containing bait and prey plasmids, but only the bait or the prey was fused to DsRed.

Surprisingly, DsRed took days at room temperature to reach full red fluorescence. At room temperature, a sample of purified protein initially showed a major component of green fluorescence (excitation and emission maxima at 475 and 499 nm, respectively), which peaked in intensity at about 7 hr and decreased to nearly zero over two days. Meanwhile, the red fluorescence reached half its maximal fluorescence after approximately 27 hr and required more than 48 hr to reach greater than 90% of maximal fluorescence (see Baird et al., supra, 2000).

Fully matured DsRed had an extinction coefficient of 75,000 $M^{-1}cm^{-1}$ at its 558 nm absorbance maximum and a fluorescence quantum yield of 0.7, which is much higher than the values of 22,500 $M^{-1}$ $cm^{-1}$ and 0.23 previously reported (Matz et al., supra, 1999). These properties make mature DsRed quite similar to rhodamine dyes in wavelength and brightness. Unlike most GFP variants, DsRed displayed negligible (<10%) pH-dependence of absorbance or fluorescence from pH 5 to 12. (see Baird et al., supra, 2000). However, acidification to pH 4-4.5 depressed both the absorbance and excitation at 558 nm relative to the shorter wavelength shoulder at 526 nm, whereas the emission spectrum was unchanged in shape. DsRed was also relatively resistant to photobleaching. When exposed to a beam of 1.2 $W/cm^2$ of approximately 540 nm light in a microscope stage, microdroplets of DsRed under oil took 1 hr to bleach 90%, whereas 20 $mW/cm^2$ of 558 nm light in a spectrofluorimeter microcuvette required 83 hr to bleach 90%. The microscope and fluorimeter measurements, respectively, gave photobleach quantum efficiencies of $1.06 \times 10^{-6}$ and $4.8 \times 10^{-7}$ (mean of $7.7 \times 10^{-7}$). Analogous microscope measurements of EGFP (S65T; SEQ ID NO: 6) and EYFP-V68L/Q69K (SEQ ID NO: 10; including Q69K) gave $3 \times 10^{-6}$ and $5 \times 10^{-5}$, respectively.

In an effort to examine the nature of the red chromophore and to identify DsRed variants useful as biological indicators, DsRed was mutagenized randomly and at specific sites predicted by sequence alignment with GFP to be near the chromophore. Many mutants that matured more slowly or not at all were identified, but none were identified that matured faster than DsRed. Screening of random mutants identified mutants that appeared green or yellow, which was found to be due to substitutions K83E, K83R, S197T, and Y120H. The green fluorescence was due to a mutant species with excitation and emission maxima at 475 and 500 nm, respectively, whereas the yellow was due to a mixture of this green species with DsRed-like material, rather than to a single species at intermediate wavelengths.

The DsRed K83R mutant had the lowest percentage conversion to red, and proved very useful as a stable version of the immature green-fluorescing form of DsRed (see Baird et al., supra, 2000). Further directed mutagenesis of K83 yielded more green and yellow mutants that were impaired in chromophore maturation. In many of the K83 mutants that matured slowly and incompletely, the red peak was at longer wavelengths than DsRed. K83M was particularly interesting because its final red-fluorescing species showed a 602 nm emission maximum, with relatively little residual green fluorescence and a respectable quantum yield, 0.44. However, its maturation was slower than that of the wild type DsRed. Y120H had a red shift similar to that of K83M and appeared to produce brighter bacterial colonies, but also maintained much more residual green fluorescence.

Spectroscopic data of the DsRed mutants are shown in Table 5. "Maturation" of protein refers to the rate of appearance of the red fluorescence over the two days after protein synthesis. Because some maturation occurs during the synthesis and purification (which take 1-2 days), numerical quantification is not accurate. A simple +/− rating system was used, wherein (−−) means very little change, (−) means a 2-5 fold increase in red fluorescence, (+) means 5-20 fold increase, and (++) indicates the wild type increase (approximately 40 fold). The red/green ratio was determined two months after protein synthesis by dividing the peak emission fluorescence obtained at 558 nm excitation by the 499 nm

TABLE 5

| Mutation | Red Species | | Green Species | | Maturation Speed | Red/Green Ratio |
| | Exc (nm) | em (nm) | exc (nm) | Em (nm) | | |
|---|---|---|---|---|---|---|
| None | 558 | 583 | 475 | 499 | ++ | 840 |
| K83R | 558 | 582 | 480 | 499 | −− | 0.05 |
| K83E | 550 | 584 | 474 | 497 | −− | 0.43 |
| K83N | 558 | 592 | 474 | 497 | − | 9.8 |
| K83P | 558 | 594 | 474 | 497 | − | 3.3 |
| K83F | 560 | 594 | 474 | 499 | −− | 0.29 |
| K83W | 562 | 594 | 478 | 501 | − | 0.44 |
| K83M | 564 | 602 | 474 | 499 | −− | 49 |
| Y120H | 562 | 600 | 478 | 499 | − | 0.4 |
| S197T | 558 | 584 | 478 | 499 | + | 53 |
| K70R | 562 | 585 | 480 | 503 | − | 13.8 |
| K70M | N/a | n/a | 480 | 499 | n/a | 0 | fluorescence obtained at 475 nm excitation from the same sample. This does not represent a molar ratio of the two species because the ratio does not correct for differences in extinction coefficient or quantum yields between the two species, or the possibility of FRET between the two species if they are in a macromolecular complex.

To determine whether Lys70 or Arg95 can form imines with the terminal carbonyl of a GFP-like chromophore (see Tsien, *Nature Biotechnol.* 17:956-957, 1999), DsRed mutants K70M, K70R, and R95K were produced. K70M remained entirely green with no red component, whereas K70R matured slowly to a slightly red-shifted red species. The spectral similarity of K70R to wild type DsRed argues against covalent incorporation of either amino acid into the chromophore. No fluorescence at any visible wavelength was detected from R95K, which might be expected because Arg95 is homologous to Arg96 of GFP, which is conserved in all fluorescent proteins characterized to date (Matz et al., supra, 1999). The failure of R95K to form a green chromophore prevented testing whether Arg95 was also required for reddening.

In view of the propensity of *Aequorea* GFP to form dimers at high concentrations in solution and in some crystal forms, and the likelihood that *Renilla* GFP forms an obligate dimer (Ward, supra, 1998), the ability of DsRed to oligomerize was examined. Initial examination of the expressed proteins by SDS-PAGE suggested that aggregates formed, in that polyhistidine-tagged proteins DsRed and DsRed K83R migrated as red and yellow-green bands, respectively, at an apparent molecular weight of greater than 110 kDa when mixed with 200 mM DTT and not heated before loading onto the gel (see Baird et al., supra, 2000). In comparison, *Aequorea* GFP, when treated similarly, ran as a fluorescent green band near its predicted monomer molecular weight of 30 kDa. The high molecular weight DsRed band was not observed when the sample was briefly boiled before electrophoresis (see Gross et al., supra, 2000). Under these conditions, a band near the predicted monomer molecular weight of 30 kDa predominated and was colorless without Coomassie staining.

To determine the oligomerization status more rigorously, the DsRed protein was subjected to analytical equilibrium centrifugation (Laue and Stafford, supra, 1999). Global curve fitting of the absorbance data determined from the radial scans of equilibrated DsRed indicated that DsRed exists as an obligate tetramer in solution (Baird et al., supra, 2000), in both low salt and physiological salt concentrations. When the data was modeled with a single-species tetramer, the fitted molecular weight was 119,083 Da, which is in excellent agreement with the theoretical molecular weight of 119,068 Da for the tetramer of polyHis-tagged DsRed. Attempts to fit the curves with alternative stoichiometries from monomer to pentamer failed to converge or gave unreasonable values for the floating variables and large, non-random residuals. The residuals for the tetramer fit were much smaller and more randomly distributed, but were somewhat further improved by extending the model to allow the obligate tetramer to dimerize into an octamer, with a fitted dissociation constant of 39 µM. Thus the 558-nm-absorbing species appears to be tetrameric over the range of monomer concentrations from 14 nM to 11 µM in vitro. The hint of octamer formation at the highest concentrations is only suggestive because the highest concentrations of tetramer achieved in the ultracentrifugation cell remained more than an order of magnitude below the fitted dissociation constant.

To confirm whether DsRed also oligomerizes in live cells, FRET analysis was performed in mammalian cells and in two hybrid assays in yeast cells. HeLa cells were transfected with wild type DsRed and imaged 24 hr later, when they contained a mixture of the immature green intermediate and the final red form. The green fluorescence was monitored intermittently before and during selective photobleaching of the red species over 49 min of intense orange illumination. If the two proteins were non-associated, bleaching the red species would be expected to have no effect on the green fluorescence. In fact, however, the green fluorescence increased by 2.7 to 5.8 fold in different cells, corresponding to FRET efficiencies of 63% to 83%. These values equal or surpass the highest FRET efficiencies ever observed between GFP mutants, 68% for cyan and yellow fluorescent proteins linked by a zinc ion-saturated zinc finger domain (Miyawaki and Tsien, supra, 2000).

Additional evidence of in vivo oligomerization was provided by the directed yeast two hybrid screen. When DsRed fusions to the Gal4 DNA binding domain and activation domain were expressed in HF7C yeast, the yeast demonstrated a his$^+$ phenotype and were able to grow without supplemental histidine, indicating that a two hybrid interaction had occurred. Neither fusion construct alone (DsRed-DNA binding domain or DsRed-activation domain) produced the his$^+$ phenotype, indicating that a DsRed-DsRed interaction, and not a non-specific DsRed-Gal4 interaction, was responsible for the positive result. In addition, the his$^+$ yeast turned blue when lysed and incubated with X-gal, suggesting that the DsRed-DsRed interaction also drove transcription of the β-galactosidase gene. Thus, two separate transcriptional measurements of the yeast two hybrid assay confirmed that DsRed associates in vivo.

This investigation of DsRed revealed a that DsRed as desirable properties, as well as some nonoptimal properties, with respect to its being useful to complement or as an alternative to GFPs. The most important favorable property identified was that DsRed has a much higher extinction coefficient and fluorescence quantum yield (0.7) than was previously reported, such that the fluorescence brightness of the mature well-folded protein is comparable to rhodamine dyes and to the best GFPs.

DsRed also is quite resistant to photobleaching by intensities typical of spectrofluorimeters (mW/cm$^2$) or microscopes with arc lamp illumination and interference filters (W/cm$^2$), showing a photobleaching quantum yield on the order of $7 \times 10^{-7}$ in both regimes. This value is significantly better than those for two of the most popular green and yellow GFP mutants, EGFP ($3 \times 10^{-6}$) and EYFP-V68L/Q69K ($5 \times 10^{-5}$). The mean number of photons that a single molecule can emit before photobleaching is the ratio of the fluorescence and photobleaching quantum yields, or $1 \times 10^6$, $2 \times 10^5$, and $1.5 \times 10^4$ for DsRed, EGFP, and EYFP-V68L/Q69K, respectively. A caveat is that the apparent photobleaching quantum yield might well increase at higher light intensities and shorter times if the molecule can be driven into dark states such as triplets or tautomers from which it can recover its fluorescence. GFPs usually show a range of such dark states (Dickson et al., *Nature* 388:355-358, 1997; Schwille et al., *Proc. Natl. Acad. Sci., USA* 97:151-156, 2000), and there is no reason to expect that DsRed will be any simpler. The photobleaching measurements described herein were made over minutes to hours, and include ample time for such recovery. In contrast, fluorescence correlation spectroscopy and flow cytometry monitor single passages of molecules through a focused laser beam within microseconds to milliseconds, such that temporary dark states that last longer than the transit time count as photobleaching, raising the apparent quantum yield for bleaching. Techniques such as laser scanning confocal microscopy, in which identified molecules are repetitively scanned, will show intermediate degrees of photobleaching depending on the time scale of illumination and recovery.

Another desirable feature of DsRed is its negligible sensitivity to pH changes over the wide range (pH 4.5 to 12). The currently available brighter GFP mutants are more readily quenched than DsRed by acidic pH. Such pH sensitivity can be exploited under controlled conditions to sense pH changes, especially inside organelles or other specific compartments (see Llopis et al., *Proc. Natl. Acad. Sci., USA* 95:6803-6808, 1998), although this feature can cause artifacts in some applications.

DsRed mutants such as K83M demonstrate that DsRed can be pushed to longer wavelengths (564 and 602 nm excitation and emission maxima), while retaining adequate quantum efficiency (0.44). The 6 nm and 19 nm bathochromic shifts correspond to 191 cm$^{-1}$ and 541 cm$^{-1}$ in energy, which are of respectable magnitude for a single amino acid change that does not modify the chromophore. A homolog of DsRed recently cloned from a sea anemone has an absorbance maximum at 572 nm and extremely weak emission at 595 nm with quantum yield <0.001; one mutant had an emission peak at 610 nm but was very dim and slow to mature (Lukyanov et al., *J. Biol. Chem.* 275:25879-25882, 2000, which is incorporated herein by reference).

Less desirable features of DsRed include its slow and incomplete maturation, and its capacity to oligomerize. A maturation time on the order of days precludes a use of DsRed as a reporter for short term gene expression studies and for applications directed to tracking fusion proteins in organisms that have short generation times or fast development. Since maturation of GFPs was considerably accelerated by mutagenesis (Heim et al., *Nature* 373:663-664, 1995, which is incorporated herein by reference), DsRed similarly can be mutagenized and variants having faster maturation times can be isolated.

Because the Lys83 mutants all permitted at least some maturation, it is unlikely that the primary amine plays a direct catalytic role for this residue, a suggestion supported by the observation that the most chemically conservative replacement, Lys to Arg, impeded red development to the greatest extent. Ser197 provided a similar result, in that the most conservative possible substitution, Ser to Thr, also significantly slowed maturation. Mutations at the Lys83 and Ser197 sites appeared several times independently in separate random mutagenesis experiments and, interestingly, Lys83 and Ser197 are replaced by Leu and Thr, respectively, in the highly homologous cyan fluorescent protein dsFP483 from the same *Discosoma* species. Either of the latter two mutations could explain why dsFP483 never turns red. Residues other than Lys83 and Ser197 also affected maturation to the red.

The multimeric nature of DsRed was demonstrated by four separate lines of evidence, including slow migration on SDS-PAGE unless pre-boiled, analytical ultracentrifugation, strong FRET from the immature green to the final red form in mammalian cells, and directed two hybrid assays in yeast using HIS3 and LacZ reporter genes. Analytical ultracentrifugation provided the clearest evidence for an obligate stoichiometry of four over the entire range of monomer concentrations assayed ($10^{-8}$ to $10^{-5}$M), with a hint that octamer formation can occur at yet higher concentrations. In addition, the tests in live cells confirmed that aggregation occurs under typical conditions of use, including the reducing environment of the cytosol and the presence of native proteins.

While oligomerization of DsRed does not preclude its use as a reporter of gene expression, it can result in artifactual results in applications where DsRed is fused to a host protein, for example, to report on the trafficking or interactions of the host protein in a cell. For a host protein of mass M without its own aggregation tendencies, fusion with DsRed can result in the formation of a complex of at least 4(M+26 kDa). Furthermore, since many proteins in signal transduction are activated by oligomerization, fusion to DsRed and consequent association can result in constitutive signaling. For host proteins that are oligomeric, fusion to DsRed can cause clashes of stoichiometry, steric conflicts of quaternary structures, or crosslinking into massive aggregates. In fact, red cameleons, i.e., fusions of cyan fluorescent protein, calmodulin, and calmodulin-binding peptide, and DsRed, are far more prone to form visible punctae in mammalian cells than the corresponding yellow cameleons with yellow fluorescent protein in place of DsRed (Miyawaki et al., *Proc. Natl. Acad. Sci., USA* 96:2135-2140, 1999).

The results disclosed in Example 1, above, indicate that variants of DsRed, like those of the GFPs, can be produced such that the propensity of the fluorescent protein to oligomerize is reduced or eliminated. Non-oligomerizing DsRed variants can be constructed and examined, for example, using a yeast two hybrid or other similar assay to identify and isolate non-aggregating mutants (see Example 1). In addition, the X-ray crystallographic structure of DsRed can be examined to confirm that optimal amino acid residues are modified to produce a non-oligomerizing form of DsRed, and to identify additional residues that can be modified so as to reduce or eliminate oligomerization.

EXAMPLE 3

DsRed Variants Having Reduced Propensity to Oligomerize

This example demonstrates that mutations corresponding to those introduced into GFP variants to reduce or eliminate oligomerization also can be made in DsRed to reduce the propensity of DsRed to form tetramers.

In view of the results described in Example 1 and guided by the DsRed crystal structure, amino acid residues were identified as potentially being involved in DsRed oligomerization. One of these amino acids, isoleucine-125 (I125), was selected because, in the oligomer, the I125 residues of the subunits were close to each other in a pairwise fashion; i.e., the side chain of I125 of the A subunit was about 4 Angstroms from the side chain of I125 of the C subunit, and the I125 residues in the B and D subunits were similarly positioned (see FIG. 1). In addition, the area in which the I125 side chains reside exhibited hydrophobicity, analogous to that identified in *Aequorea* GFP variants, which was demonstrated to be involved in the inter-subunit interaction (see Example 1). Based on these observations, DsRed mutants containing substitutions of positively charged amino acids, Lys (K) and Arg (R), for I125 were generated.

DsRed I125K and I125R were prepared with the QuickChange Mutagenesis Kit (see Example 1) using the DsRed cDNA (SEQ ID NO: 11; Clontech) subcloned into the expression vector pRSETB (Invitrogen) as the template for mutagenesis. The primers for mutagenesis, with the mutated codons underlined, were as follows:

```
I125K (forward)
5'-TAC AAG GTG AAG TTC AAG GGC GTG (SEQ ID NO: 22)
AAC TTC CCC-3';

I125K (reverse)
5'-GGG GAA GTT CAC GCC CTT GAA CTT (SEQ ID NO: 23)
CAC CTT GTA-3';

I125R (forward)
5'-TAC AAG GTG AAG TTC CGC GGC GTG (SEQ ID NO: 24)
AAC TTC CCC-3';
and I125R (reverse)
5'-GGG GAA GTT CAC GCC GCG GAA CTT (SEQ ID NO: 25)
CAC CTT GTA-3'.
```

The mutant proteins were prepared following standard methodology and analyzed with polyacrylamide gel electrophoresis as described (Baird et al., supra, 2000). For further analysis, DsRed I125R was dialyzed extensively in PBS, then diluted in PBS until the absorbance of the solution at 558 nm was 0.1. This solution was centrifuged in a Beckman XL-1 analytical ultracentrifuge in PBS at 10,000 rpm, 12,000 rpm, 14,000 rpm, and 20,000 rpm. Absorbance at 558 nm versus radius was determined and compared to a wild type tetrameric DsRed control (Baird et al., supra, 2000).

The DsRed I125K yielded a protein that became red fluorescent and was a mixture of dimer and tetramer as analyzed by non-denaturing polyacrylamide gel electrophoresis of the native protein. The same analysis of Ds Red I125R revealed that the protein was entirely dimeric. The dimeric status of DsRed I125R was confirmed by analytical ultracentrifugation; no residual tetramer was detected. These results demonstrate that the interaction between the A:C subunits and the B:D subunits can be disrupted, thereby reducing the propensity of the DsRed variant to oligomerize (see FIG. 1). No attempt was made to disrupt the A:B and C:D interfaces. These results demonstrate that the method of reducing or eliminating oligomerization of the GFP variants as described in Example 1 is generally applicable to other fluorescent proteins that have a propensity to oligomerize.

EXAMPLE 4

Preparation and Characterization of Non-oligomerizing Tandem DsRed

This example demonstrates that a tandem DsRed protein can be formed by linking two DsRed monomers, and that such tandem DsRed proteins maintain emission and excitation spectra characteristic of DsRed, but do not oligomerize.

To construct tDsRed, a 3' primer, 5'-CCGGATCCCCTTTGGTGCTGCCCTCTCCGCTGC-CAGGCTTGCCGCTG CCGCTGGTGCTGCCAAGGAA-CAGATGGTGGCGTCCCTCG-3' (SEQ ID NO:27), was designed that overlapped the last 25 bp of DsRed (derived from the Clontech vector pDsRed-N1) and encoded for the linker sequence GSTSGSGKPGSGEGSTKG (SEQ ID NO:26), followed by a Bam HI restriction site in frame with the Bam HI site of pRSET$_B$ (Invitrogen). It was later determined that the above primer sequence contains three mismatches in the overlap region and contained several codons that were not optimal for mammalian expression. Accordingly, a new 3' primer, 5'-CCGGATCCCCCTTGGT-GCTGCCCTCCCCGCTGCCGGGCTTCCCGCTC CCGCTGGTGCTGCCCAGGAACAGGTG-GTGGCGGCCCTCG-3' (SEQ ID NO:28), also was used. The 5' primer, 5'-GTACGA CGATGACGATAAGGATCC-3' (SEQ ID NO:29) also contained a Bam HI restriction site in frame with the Bam HI site of pRSET$_B$.

PCR amplification of DsRed and of DsRed-I125R with the new linker was accomplished with Taq DNA polymerase (Roche) and an annealing protocol that included 2 cycles at 40° C., 5 cycles at 43° C., 5 cycles at 45° C., and 15 cycles at 52° C. The resulting PCR product was purified by agarose gel-electrophoresis and digested with Bam HI (New England Biolabs). Bam HI and calf intestinal phosphatase (New England Biolabs) treated vector was prepared from pRSET$_B$ with DsRed or DsRed-I125R inserted in frame with the His-6 tag and between the 5' Bam HI and 3' Eco RI restriction sites.

Following ligation of the digested PCR products and vector with T4 DNA ligase (NEB), the mixture was used to transform competent *E. coli* DH5α by heat shock. Transformed colonies were grown on LB agar plates supplemented with the antibiotic ampicillin. Colonies were picked at random, and plasmid DNA was isolated through standard miniprep procedures (Qiagen). DNA sequencing was used to confirm the correct orientation of the inserted sequence.

In order to express protein, the isolated and sequenced vectors were used to transform competent *E. coli* JM109 (DE3). Single colonies grown on LB agar/ampicillin were used to inoculate 1 liter cultures of LB/ampicillin, then were grown with shaking at 225 rpm and 37° C. until the broth reached an OD$_{600}$ of 0.5-1.0. IPTG was added to a final concentration of 100 mg/l and the culture was grown for either 5 hr at 37° C. (tDsRed) or 24 hr at room temperature (RT; tDsRed-I125R). Cells were harvested by centrifugation (10 min, 5000 rpm), the pellet was resuspended in 50 mM Tris pH 7.5, and the cells were lysed by a single pass through a French press. Protein was purified by Ni-NTA (Qiagen) chromatography as described by the manufacturer and was stored in the elution buffer or was dialyzed into 50 mM Tris, pH 7.5.

With respect to the excitation and emission spectra as well as the maturation time of tDsRed and tDsRed-I125R, the proteins behaved identically to their untethered counterparts. As expected, tDsRed developed visible fluorescence within approximately 12 hr at RT, while tDsRed-I125R required several days before significant red color developed. The maturation of tDsRed-I125R continued for up to approximately 10 days. The excitation and emission maxima were unchanged at 558 nm and 583 nm, respectively.

The differences in the tandem dimer became apparent when the proteins were analyzed by SDS-polyacrylamide electrophoresis. Due to the high stability of the tetramer, DsRed that was not subjected to boiling migrated with an apparent molecular mass of about 110 kDa. In addition, the band on the gel, which corresponded to a DsRed tetramer, retained its red fluorescence, indicating that the rigid barrel structure of each monomer was intact. When the sample was boiled before loading, DsRed was non-fluorescent and presumably denatured, and ran as a monomer of approximately 32 kDa.

SDS-PAGE analysis confirmed the tandem structure of the expressed red fluorescent proteins, tDsRed and tDsRed-I125R. The unboiled tDsRed migrated at the same apparent molecular mass (about 110 kDa) as unboiled normal DsRed. The difference in their molecular structures only was apparent when the samples were boiled (denatured) before they were loaded onto the gel. Boiled tDsRed migrated with an apparent molecular mass of about 65 kDa, which is approximately the mass of two DsRed monomers, whereas boiled DsRed migrated at the monomer molecular mass of 32 kDa.

A similar comparison was made for DsRed-I125R and tDsRed-I125R. When they were not boiled prior to SDS-PAGE, tDsRed-I125R and DsRed-I125R both migrated as dimers with an apparent molecular mass of about 50 kDa. DsRed-I125R that was not boiled also had a large component that appeared to be denatured, though the fluorescent band for the dimer (50 kDa) was clearly visible. tDsRed-I125R also had a denatured component that migrated slower (65 kDa vs. 50 kDa) than the intact fluorescent species. However, when boiled, tDsRed-I125R migrated at approximately the same mass as two monomers (65 kDa), while DsRed-I125R migrated at the monomer molecular mass of 32 kDa.

These results demonstrate that linking two DsRed monomers to form an intramolecularly bound tandem dimer prevented formation of intermolecular oligomers, without affecting the emission or excitation spectra of the red fluorescent proteins.

Although the invention has been described with reference to the above examples, it will be understood that modifications and variations are encompassed within the spirit and scope of the invention. Accordingly, the invention is limited only by the following claims.

What is claimed is:

1. An isolated polynucleotide encoding at least a first monomer of a non-oligomerizing tandem fluorescent protein, said non-oligomerizing tandem fluorescent protein comprising a plurality of monomers, wherein the non-oligomerizing tandem fluorescent protein comprises a first monomer of an Aequorea green fluorescent protein (GFP; SEQ ID NO: 2) or a fluorescent protein of SEQ ID NO: 6 or SEQ ID NO: 10 operatively linked to at least a second monomer of the Aequorea GFP (SEQ ID NO: 2) or the fluorescent protein of SEQ ID NO: 6 or SEQ ID NO: 10, wherein said first monomer of the tandem fluorescent protein comprises a mutation substituting an amino acid having a positively charged side-chain for an amino acid residue corresponding to A206, L221, F223, or a combination thereof of SEQ ID NO: 2, SEQ ID NO: 6 or SEQ ID NO: 10, wherein the numbering of the amino acid residues conforms to that in native Aequorea GFP (SEQ ID NO: 2), and wherein the propensity of the tandem fluorescent protein to form intermolecular oligomers is reduced or inhibited as compared to a monomer of the Aequorea GFP (SEQ ID NO: 2) or the fluorescent protein of SEQ ID NO: 6 or SEQ ID NO: 10.

2. The isolated polynucleotide of claim 1, wherein the mutation corresponds to an A206K mutation, an L221K mutation, an F223R mutation, or an L221K and F223R mutation of SEQ ID NO: 6 or SEQ ID NO: 10.

3. The isolated polynucleotide of claim 1, wherein the first monomer and the second monomer are operatively linked using a peptide linker.

4. The isolated polynucleotide of claim 1, further comprising at least a third monomer of the fluorescent protein, which is operatively linked to the first monomer or the second monomer.

5. An isolated polynucleotide encoding at least a first monomer of a fusion protein, wherein the fusion protein comprises the non-oligomerizing tandem fluorescent protein of claim 1 operatively linked to at least one polypeptide of interest.

6. The isolated polynucleotide of claim 5, wherein the non-oligomerizing tandem fluorescent protein is linked to the polypeptide of interest through a peptide bond.

7. The isolated polynucleotide of claim 5, wherein the non-oligomerizing tandem fluorescent protein is linked to the polypeptide of interest through a peptide linker.

8. The isolated polynucleotide of claim 5, wherein at least one polypeptide of interest comprises a peptide tag.

9. The isolated polynucleotide of claim 8, wherein the peptide tag is a polyhistidine peptide.

10. The isolated polynucleotide of claim 5, wherein at least one polypeptide of interest is a cellular polypeptide.

11. The isolated polynucleotide of claim 10, wherein the polypeptide of interest is a cellular polypeptide selected from an enzyme, a G-protein, a growth factor receptor, or a transcription factor.

12. The isolated polynucleotide of claim 5, wherein the polypeptide of interest is one of two or more proteins that associate to form a complex.

13. A vector comprising the isolated polynucleotide of claim 1.

14. A host cell comprising the isolated polynucleotide of claim 1.

15. A kit comprising at least one isolated polynucleotide of claim 1.

16. A polynucleotide of claim 1, wherein the mutated first monomer of the Aeguorea GFP (SEQ ID NO: 2) further comprises amino acid mutations S65G, S72A, T203Y, and H231L.

17. A polynucleotide of claim 1, wherein the mutated first monomer of the Aeguorea GFP (SEQ ID NO: 2) further comprising amino acid mutations S65G, V68L, Q69K, S72A, T203Y, and H231L.

18. A polynucleotide of claim 1, wherein the mutated first monomer of the Aeguorea GFP (SEQ ID NO: 2) further comprises amino acid mutations K26R, F64L, S65T, Y66W, N146I, M153T, V163A, N164H, and H231L.

19. A polynucleotide of claim 1, wherein the mutated first monomer of the Aeauorea GFP (SEQ ID NO: 2) further comprises amino acid mutations F64L, S65T, and H231L.

20. A polynucleotide of claim 1, wherein the mutated first monomer of the Aequorea GFP (SEQ ID NO: 2) further comprises amino acid mutations H148G or H148Q.

* * * * *

SEQUENCE LISTING

<160> NUMBER OF SEQ ID NOS: 29

<210> SEQ ID NO 1
<211> LENGTH: 716
<212> TYPE: DNA
<213> ORGANISM: Aequorea victoria
<220> FEATURE:
<221> NAME/KEY: CDS
<222> LOCATION: (1)..(714)

<400> SEQUENCE: 1

| | | | | | | | | | | | | | | | | |
|---|---|---|---|---|---|---|---|---|---|---|---|---|---|---|---|---|
| atg | agt | aaa | gga | gaa | gaa | ctt | ttc | act | gga | gtt | gtc | cca | att | ctt | gtt | 48 |
| Met | Ser | Lys | Gly | Glu | Glu | Leu | Phe | Thr | Gly | Val | Val | Pro | Ile | Leu | Val | |
| 1 | | | | 5 | | | | | 10 | | | | | 15 | | |

| gaa | tta | gat | ggt | gat | gtt | aat | ggg | cac | aaa | ttt | tct | gtc | agt | gga | gag | 96 |
|---|---|---|---|---|---|---|---|---|---|---|---|---|---|---|---|---|
| Glu | Leu | Asp | Gly | Asp | Val | Asn | Gly | His | Lys | Phe | Ser | Val | Ser | Gly | Glu | |
| | | | 20 | | | | | 25 | | | | | 30 | | | |

| ggt | gaa | ggt | gat | gca | aca | tac | gga | aaa | ctt | acc | ctt | aaa | ttt | att | tgc | 144 |
|---|---|---|---|---|---|---|---|---|---|---|---|---|---|---|---|---|
| Gly | Glu | Gly | Asp | Ala | Thr | Tyr | Gly | Lys | Leu | Thr | Leu | Lys | Phe | Ile | Cys | |
| | | 35 | | | | | 40 | | | | | 45 | | | | |

| act | act | gga | aaa | cta | cct | gtt | cca | tgg | cca | aca | ctt | gtc | act | act | ttc | 192 |
|---|---|---|---|---|---|---|---|---|---|---|---|---|---|---|---|---|
| Thr | Thr | Gly | Lys | Leu | Pro | Val | Pro | Trp | Pro | Thr | Leu | Val | Thr | Thr | Phe | |
| 50 | | | | | 55 | | | | | 60 | | | | | | |

| tct | tat | ggt | gtt | caa | tgc | ttt | tca | aga | tac | cca | gat | cat | atg | aaa | cag | 240 |
|---|---|---|---|---|---|---|---|---|---|---|---|---|---|---|---|---|
| Ser | Tyr | Gly | Val | Gln | Cys | Phe | Ser | Arg | Tyr | Pro | Asp | His | Met | Lys | Gln | |
| 65 | | | | 70 | | | | | 75 | | | | | 80 | | |

| cat | gac | ttt | ttc | aag | agt | gcc | atg | ccc | gaa | ggt | tat | gta | cag | gaa | aga | 288 |
|---|---|---|---|---|---|---|---|---|---|---|---|---|---|---|---|---|
| His | Asp | Phe | Phe | Lys | Ser | Ala | Met | Pro | Glu | Gly | Tyr | Val | Gln | Glu | Arg | |
| | | | | 85 | | | | | 90 | | | | | 95 | | |

| act | ata | ttt | ttc | aaa | gat | gac | ggg | aac | tac | aag | aca | cgt | gct | gaa | gtc | 336 |
|---|---|---|---|---|---|---|---|---|---|---|---|---|---|---|---|---|
| Thr | Ile | Phe | Phe | Lys | Asp | Asp | Gly | Asn | Tyr | Lys | Thr | Arg | Ala | Glu | Val | |
| | | | 100 | | | | | 105 | | | | | 110 | | | |

| aag | ttt | gaa | ggt | gat | acc | ctt | gtt | aat | aga | atc | gag | tta | aaa | ggt | att | 384 |
|---|---|---|---|---|---|---|---|---|---|---|---|---|---|---|---|---|
| Lys | Phe | Glu | Gly | Asp | Thr | Leu | Val | Asn | Arg | Ile | Glu | Leu | Lys | Gly | Ile | |
| | | 115 | | | | | 120 | | | | | 125 | | | | |

| gat | ttt | aaa | gaa | gat | gga | aac | att | ctt | gga | cac | aaa | ttg | gaa | tac | aac | 432 |
|---|---|---|---|---|---|---|---|---|---|---|---|---|---|---|---|---|
| Asp | Phe | Lys | Glu | Asp | Gly | Asn | Ile | Leu | Gly | His | Lys | Leu | Glu | Tyr | Asn | |
| 130 | | | | | 135 | | | | | 140 | | | | | | |

| tat | aac | tca | cac | aat | gta | tac | atc | atg | gca | gac | aaa | caa | aag | aat | gga | 480 |
|---|---|---|---|---|---|---|---|---|---|---|---|---|---|---|---|---|
| Tyr | Asn | Ser | His | Asn | Val | Tyr | Ile | Met | Ala | Asp | Lys | Gln | Lys | Asn | Gly | |
| 145 | | | | 150 | | | | | 155 | | | | | 160 | | |

| atc | aaa | gtt | aac | ttc | aaa | att | aga | cac | aac | att | gaa | gat | gga | agc | gtt | 528 |
|---|---|---|---|---|---|---|---|---|---|---|---|---|---|---|---|---|
| Ile | Lys | Val | Asn | Phe | Lys | Ile | Arg | His | Asn | Ile | Glu | Asp | Gly | Ser | Val | |
| | | | 165 | | | | | 170 | | | | | 175 | | | |

| caa | cta | gca | gac | cat | tat | caa | caa | aat | act | cca | att | ggc | gat | ggc | cct | 576 |
|---|---|---|---|---|---|---|---|---|---|---|---|---|---|---|---|---|
| Gln | Leu | Ala | Asp | His | Tyr | Gln | Gln | Asn | Thr | Pro | Ile | Gly | Asp | Gly | Pro | |
| | | | 180 | | | | | 185 | | | | | 190 | | | |

| gtc | ctt | tta | cca | gac | aac | cat | tac | ctg | tcc | aca | caa | tct | gcc | ctt | tcg | 624 |
|---|---|---|---|---|---|---|---|---|---|---|---|---|---|---|---|---|
| Val | Leu | Leu | Pro | Asp | Asn | His | Tyr | Leu | Ser | Thr | Gln | Ser | Ala | Leu | Ser | |
| | | 195 | | | | | 200 | | | | | 205 | | | | |

| aaa | gat | ccc | aac | gaa | aag | aga | gac | cac | atg | gtc | ctt | ctt | gag | ttt | gta | 672 |
|---|---|---|---|---|---|---|---|---|---|---|---|---|---|---|---|---|
| Lys | Asp | Pro | Asn | Glu | Lys | Arg | Asp | His | Met | Val | Leu | Leu | Glu | Phe | Val | |
| | 210 | | | | | 215 | | | | | 220 | | | | | |

| aca | gct | gct | ggg | att | aca | cat | ggc | atg | gat | gaa | cta | tac | aaa | ta | | 716 |
|---|---|---|---|---|---|---|---|---|---|---|---|---|---|---|---|---|
| Thr | Ala | Ala | Gly | Ile | Thr | His | Gly | Met | Asp | Glu | Leu | Tyr | Lys | | | |
| 225 | | | | | 230 | | | | | 235 | | | | | | |

<210> SEQ ID NO 2
<211> LENGTH: 238
<212> TYPE: PRT

<213> ORGANISM: Aequorea victoria

<400> SEQUENCE: 2

| Met | Ser | Lys | Gly | Glu | Glu | Leu | Phe | Thr | Gly | Val | Val | Pro | Ile | Leu | Val |
| 1 | | | | 5 | | | | | 10 | | | | | 15 | |

| Glu | Leu | Asp | Gly | Asp | Val | Asn | Gly | His | Lys | Phe | Ser | Val | Ser | Gly | Glu |
| | | | 20 | | | | | 25 | | | | | 30 | | |

| Gly | Glu | Gly | Asp | Ala | Thr | Tyr | Gly | Lys | Leu | Thr | Leu | Lys | Phe | Ile | Cys |
| | | 35 | | | | | 40 | | | | | 45 | | | |

| Thr | Thr | Gly | Lys | Leu | Pro | Val | Pro | Trp | Pro | Thr | Leu | Val | Thr | Thr | Phe |
| | 50 | | | | | 55 | | | | | 60 | | | | |

| Ser | Tyr | Gly | Val | Gln | Cys | Phe | Ser | Arg | Tyr | Pro | Asp | His | Met | Lys | Gln |
| 65 | | | | | 70 | | | | | 75 | | | | | 80 |

| His | Asp | Phe | Phe | Lys | Ser | Ala | Met | Pro | Glu | Gly | Tyr | Val | Gln | Glu | Arg |
| | | | | 85 | | | | | 90 | | | | | 95 | |

| Thr | Ile | Phe | Phe | Lys | Asp | Asp | Gly | Asn | Tyr | Lys | Thr | Arg | Ala | Glu | Val |
| | | | | 100 | | | | | 105 | | | | | 110 | |

| Lys | Phe | Glu | Gly | Asp | Thr | Leu | Val | Asn | Arg | Ile | Glu | Leu | Lys | Gly | Ile |
| | | | 115 | | | | | 120 | | | | | 125 | | |

| Asp | Phe | Lys | Glu | Asp | Gly | Asn | Ile | Leu | Gly | His | Lys | Leu | Glu | Tyr | Asn |
| | | 130 | | | | | 135 | | | | | 140 | | | |

| Tyr | Asn | Ser | His | Asn | Val | Tyr | Ile | Met | Ala | Asp | Lys | Gln | Lys | Asn | Gly |
| 145 | | | | | 150 | | | | | 155 | | | | | 160 |

| Ile | Lys | Val | Asn | Phe | Lys | Ile | Arg | His | Asn | Ile | Glu | Asp | Gly | Ser | Val |
| | | | | 165 | | | | | 170 | | | | | 175 | |

| Gln | Leu | Ala | Asp | His | Tyr | Gln | Gln | Asn | Thr | Pro | Ile | Gly | Asp | Gly | Pro |
| | | | 180 | | | | | 185 | | | | | 190 | | |

| Val | Leu | Leu | Pro | Asp | Asn | His | Tyr | Leu | Ser | Thr | Gln | Ser | Ala | Leu | Ser |
| | | | 195 | | | | | 200 | | | | | 205 | | |

| Lys | Asp | Pro | Asn | Glu | Lys | Arg | Asp | His | Met | Val | Leu | Leu | Glu | Phe | Val |
| | | | 210 | | | | | 215 | | | | | 220 | | |

| Thr | Ala | Ala | Gly | Ile | Thr | His | Gly | Met | Asp | Glu | Leu | Tyr | Lys | | |
| 225 | | | | | 230 | | | | | 235 | | | | | |

<210> SEQ ID NO 3
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 3

| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |

| gtc | gag | ctg | gac | ggc | gac | gta | aac | ggc | cac | aag | ttc | agc | gtg | tcc | ggc | 96 |
| Val | Glu | Leu | Asp | Gly | Asp | Val | Asn | Gly | His | Lys | Phe | Ser | Val | Ser | Gly | |
| | | | 20 | | | | | 25 | | | | | 30 | | | |

| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | | 35 | | | | | 40 | | | | | 45 | | | | |

| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| | 50 | | | | | 55 | | | | | 60 | | | | | |

| ctg | acc | tac | ggc | gtg | cag | tgc | ttc | agc | cgc | tac | ccc | gac | cac | atg | aag | 240 |
| Leu | Thr | Tyr | Gly | Val | Gln | Cys | Phe | Ser | Arg | Tyr | Pro | Asp | His | Met | Lys | |
| 65 | | | | | 70 | | | | | 75 | | | | | 80 | |

```
cag cac gac ttc ttc aag tcc gcc atg ccc gaa ggc tac gtc cag gag       288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag       336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc       384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac       432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac       480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc       528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc       576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg       624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc       672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa       720
Val Thr Ala Ala Gly Ile Thr Leu Gly Met Asp Glu Leu Tyr Lys
225                 230                 235

<210> SEQ ID NO 4
<211> LENGTH: 239
<212> TYPE: PRT
<213> ORGANISM: Aequorea victoria

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 5
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 5
```

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |
| gtc | gag | ctg | gac | ggc | gac | gta | aac | ggc | cac | agg | ttc | agc | gtg | tcc | ggc | 96 |
| Val | Glu | Leu | Asp | Gly | Asp | Val | Asn | Gly | His | Arg | Phe | Ser | Val | Ser | Gly | |
| | | | 20 | | | | | 25 | | | | | 30 | | | |
| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | | 35 | | | | | 40 | | | | | 45 | | | | |
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| | 50 | | | | | 55 | | | | | 60 | | | | | |
| ctg | acc | tgg | ggc | gtg | cag | tgc | ttc | agc | cgc | tac | ccc | gac | cac | atg | aag | 240 |
| Leu | Thr | Trp | Gly | Val | Gln | Cys | Phe | Ser | Arg | Tyr | Pro | Asp | His | Met | Lys | |
| 65 | | | | | 70 | | | | | 75 | | | | | 80 | |
| cag | cac | gac | ttc | ttc | aag | tcc | gcc | atg | ccc | gaa | ggc | tac | gtc | cag | gag | 288 |
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |
| cgt | acc | atc | ttc | ttc | aag | gac | gac | ggc | aac | tac | aag | acc | cgc | gcc | gag | 336 |
| Arg | Thr | Ile | Phe | Phe | Lys | Asp | Asp | Gly | Asn | Tyr | Lys | Thr | Arg | Ala | Glu | |
| | | | 100 | | | | | 105 | | | | | 110 | | | |
| gtg | aag | ttc | gag | ggc | gac | acc | ctg | gtg | aac | cgc | atc | gag | ctg | aag | ggc | 384 |
| Val | Lys | Phe | Glu | Gly | Asp | Thr | Leu | Val | Asn | Arg | Ile | Glu | Leu | Lys | Gly | |
| | | 115 | | | | | 120 | | | | | 125 | | | | |
| atc | gac | ttc | aag | gag | gac | ggc | aac | atc | ctg | ggg | cac | aag | ctg | gag | tac | 432 |
| Ile | Asp | Phe | Lys | Glu | Asp | Gly | Asn | Ile | Leu | Gly | His | Lys | Leu | Glu | Tyr | |
| | 130 | | | | | 135 | | | | | 140 | | | | | |
| aac | tac | atc | agc | cac | aac | gtc | tat | atc | acc | gcc | gac | aag | cag | aag | aac | 480 |
| Asn | Tyr | Ile | Ser | His | Asn | Val | Tyr | Ile | Thr | Ala | Asp | Lys | Gln | Lys | Asn | |
| 145 | | | | | 150 | | | | | 155 | | | | | 160 | |
| ggc | atc | aag | gcc | cac | ttc | aag | atc | cgc | cac | aac | atc | gag | gac | ggc | agc | 528 |
| Gly | Ile | Lys | Ala | His | Phe | Lys | Ile | Arg | His | Asn | Ile | Glu | Asp | Gly | Ser | |
| | | | | 165 | | | | | 170 | | | | | 175 | | |
| gtg | cag | ctc | gcc | gac | cac | tac | cag | cag | aac | acc | ccc | atc | ggc | gac | ggc | 576 |
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |
| ccc | gtg | ctg | ctg | ccc | gac | aac | cac | tac | ctg | agc | acc | cag | tcc | gcc | ctg | 624 |
| Pro | Val | Leu | Leu | Pro | Asp | Asn | His | Tyr | Leu | Ser | Thr | Gln | Ser | Ala | Leu | |
| | | 195 | | | | | 200 | | | | | 205 | | | | |
| agc | aaa | gac | ccc | aac | gag | aag | cgc | gat | cac | atg | gtc | ctg | ctg | gag | ttc | 672 |

```
Ser Lys Asp Pro Asn Glu Lys Arg Asp His Met Val Leu Leu Glu Phe
    210             215                 220 gtg acc gcc gcc ggg atc act ctc ggc atg gac gag ctg tac aag taa          720
Val Thr Ala Ala Gly Ile Thr Leu Gly Met Asp Glu Leu Tyr Lys
225                 230                 235
```

<210> SEQ ID NO 6
<211> LENGTH: 239
<212> TYPE: PRT
<213> ORGANISM: Aequorea victoria

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 7
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 7

```
atg gtg agc aag ggc gag gag ctg ttc acc ggg gtg gtg ccc atc ctg     48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc     96
Val Glu Leu Asp Gly Asp Val Asn Gly His Lys Phe Ser Val Ser Gly
            20                  25                  30
```

```
gag ggc gag ggc gat gcc acc tac ggc aag ctg acc ctg aag ttc atc       144
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc       192
Cys Thr Thr Gly Lys Leu Pro Val Pro Trp Pro Thr Leu Val Thr Thr
 50                  55                  60 ttc ggc tac ggc gtg cag tgc ttc gcc cgc tac ccc gac cac atg aag       240
Phe Gly Tyr Gly Val Gln Cys Phe Ala Arg Tyr Pro Asp His Met Lys
 65                  70                  75                  80 cag cac gac ttc ttc aag tcc gcc atg ccc gaa ggc tac gtc cag gag       288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag       336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc       384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac       432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac       480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc       528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc       576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg       624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc       672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa      720
Val Thr Ala Ala Gly Ile Thr Leu Gly Met Asp Glu Leu Tyr Lys
225                 230                 235
```

<210> SEQ ID NO 8
<211> LENGTH: 239
<212> TYPE: PRT
<213> ORGANISM: Aequorea victoria

<400> SEQUENCE: 8

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Phe Gly Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110
```

```
                 100                 105                 110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 9
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 9 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ttc ggc tac ggc ctg aag tgc ttc gcc cgc tac ccc gac cac atg aag     240
Phe Gly Tyr Gly Leu Lys Cys Phe Ala Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
```

-continued

```
                165                 170                 175
gtg cag ctc gcc gac cac tac cag cag aac acc ccc atc ggc gac ggc      576
Val Gln Leu Ala Asp His Tyr Gln Gln Asn Thr Pro Ile Gly Asp Gly
        180                 185                 190 ccc gtg ctg ctg ccc gac aac cac tac ctg agc tac cag tcc gcc ctg      624
Pro Val Leu Leu Pro Asp Asn His Tyr Leu Ser Tyr Gln Ser Ala Leu
    195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
210                 215                 220 gtg acc gcc gcc ggg atc act ctc ggc atg gac gag ctg tac aag taa      720
Val Thr Ala Ala Gly Ile Thr Leu Gly Met Asp Glu Leu Tyr Lys
225                 230                 235
```

<210> SEQ ID NO 10
<211> LENGTH: 239
<212> TYPE: PRT
<213> ORGANISM: Aequorea victoria

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 11
<211> LENGTH: 859
<212> TYPE: DNA
<213> ORGANISM: Discosoma sp.
<220> FEATURE:
<221> NAME/KEY: CDS
<222> LOCATION: (54)..(731)

<400> SEQUENCE: 11

```
gtttcagcca gtgacggtca gtgacagggt gagccacttg gtataccaac aaa atg        56
                                                             Met
                                                             1 agg tct tcc aag aat gtt atc aag gag ttc atg agg ttt aag gtt cgc       104
Arg Ser Ser Lys Asn Val Ile Lys Glu Phe Met Arg Phe Lys Val Arg
          5                  10                  15 atg gaa gga acg gtc aat ggg cac gag ttt gaa ata gaa ggc gaa gga       152
Met Glu Gly Thr Val Asn Gly His Glu Phe Glu Ile Glu Gly Glu Gly
             20                  25                  30 gag ggg agg cca tac gaa ggc cac aat acc gta aag ctt aag gta acc       200
Glu Gly Arg Pro Tyr Glu Gly His Asn Thr Val Lys Leu Lys Val Thr
 35                  40                  45 aag ggg gga cct ttg cca ttt gct tgg gat att ttg tca cca caa ttt       248
Lys Gly Gly Pro Leu Pro Phe Ala Trp Asp Ile Leu Ser Pro Gln Phe
 50                  55                  60                  65 cag tat gga agc aag gta tat gtc aag cac cct gcc gac ata cca gac       296
Gln Tyr Gly Ser Lys Val Tyr Val Lys His Pro Ala Asp Ile Pro Asp
                 70                  75                  80 tat aaa aag ctg tca ttt cct gaa gga ttt aaa tgg gaa agg gtc atg       344
Tyr Lys Lys Leu Ser Phe Pro Glu Gly Phe Lys Trp Glu Arg Val Met
             85                  90                  95 aac ttt gaa gac ggt ggc gtc gtt act gta acc cag gat tcc agt ttg       392
Asn Phe Glu Asp Gly Gly Val Val Thr Val Thr Gln Asp Ser Ser Leu
        100                 105                 110 cag gat ggc tgt ttc atc tac aag gtc aag ttc att ggc gtg aac ttt       440
Gln Asp Gly Cys Phe Ile Tyr Lys Val Lys Phe Ile Gly Val Asn Phe
    115                 120                 125 cct tcc gat gga cct gtt atg caa aag aag aca atg ggc tgg gaa gcc       488
Pro Ser Asp Gly Pro Val Met Gln Lys Lys Thr Met Gly Trp Glu Ala
130                 135                 140                 145 agc act gag cgt ttg tat cct cgt gat ggc gtg ttg aaa gga gag att       536
Ser Thr Glu Arg Leu Tyr Pro Arg Asp Gly Val Leu Lys Gly Glu Ile
                150                 155                 160 cat aag gct ctg aag ctg aaa gac ggt ggt cat tac cta gtt gaa ttc       584
His Lys Ala Leu Lys Leu Lys Asp Gly Gly His Tyr Leu Val Glu Phe
            165                 170                 175 aaa agt att tac atg gca aag aag cct gtg cag cta cca ggg tac tac       632
Lys Ser Ile Tyr Met Ala Lys Lys Pro Val Gln Leu Pro Gly Tyr Tyr
        180                 185                 190 tat gtt gac tcc aaa ctg gat ata aca agc cac aac gaa gac tat aca       680
Tyr Val Asp Ser Lys Leu Asp Ile Thr Ser His Asn Glu Asp Tyr Thr
    195                 200                 205 atc gtt gag cag tat gaa aga acc gag gga cgc cac cat ctg ttc ctt       728
Ile Val Glu Gln Tyr Glu Arg Thr Glu Gly Arg His His Leu Phe Leu
210                 215                 220                 225 taa ggctgaactt ggctcagacg tgggtgagcg gtaatgacca caaaaggcag            781
cgaagaaaaa ccatgatcgt ttttttttagg ttggcagcct gaaatcgtag gaaatacatc   841
agaaatgtta caaacagg                                                   859
```

<210> SEQ ID NO 12
<211> LENGTH: 225
<212> TYPE: PRT
<213> ORGANISM: Discosoma sp.

<400> SEQUENCE: 12

```
Met Arg Ser Ser Lys Asn Val Ile Lys Glu Phe Met Arg Phe Lys Val
1               5                   10                  15
```

Arg Met Glu Gly Thr Val Asn Gly His Glu Phe Glu Ile Glu Gly Glu
                 20                  25                  30

Gly Glu Gly Arg Pro Tyr Glu Gly His Asn Thr Val Lys Leu Lys Val
             35                  40                  45

Thr Lys Gly Gly Pro Leu Pro Phe Ala Trp Asp Ile Leu Ser Pro Gln
         50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
             100                 105                 110

Leu Gln Asp Gly Cys Phe Ile Tyr Lys Val Lys Phe Ile Gly Val Asn
         115                 120                 125

Phe Pro Ser Asp Gly Pro Val Met Gln Lys Lys Thr Met Gly Trp Glu
     130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                 165                 170                 175

Phe Lys Ser Ile Tyr Met Ala Lys Lys Pro Val Gln Leu Pro Gly Tyr
             180                 185                 190

Tyr Tyr Val Asp Ser Lys Leu Asp Ile Thr Ser His Asn Glu Asp Tyr
         195                 200                 205

Thr Ile Val Glu Gln Tyr Glu Arg Thr Glu Gly Arg His His Leu Phe
     210                 215                 220

Leu
225

<210> SEQ ID NO 13
<211> LENGTH: 42
<212> TYPE: DNA
<213> ORGANISM: Artificial Sequence
<220> FEATURE:
<223> OTHER INFORMATION: PRIMER A206K top

<400> SEQUENCE: 13
cagtccaagc tgagcaaaga ccccaacgag aagcgcgatc ac                          42

<210> SEQ ID NO 14
<211> LENGTH: 42
<212> TYPE: DNA
<213> ORGANISM: Artificial Sequence
<220> FEATURE:
<223> OTHER INFORMATION: PRIMER A206K bottom

<400> SEQUENCE: 14
gtgatcgcgc ttctcgttgg ggtctttgct cagcttggac tg                          42

<210> SEQ ID NO 15
<211> LENGTH: 36
<212> TYPE: DNA
<213> ORGANISM: Artificial Sequence
<220> FEATURE:
<223> OTHER INFORMATION: PRIMER L221K top

<400> SEQUENCE: 15
cacatggtcc tgaaggagtt cgtgaccgcc gccggg                                 36

```
<210> SEQ ID NO 16
<211> LENGTH: 36
<212> TYPE: DNA
<213> ORGANISM: Artificial Sequence
<220> FEATURE:
<223> OTHER INFORMATION: PRIMER L221K bottom

<400> SEQUENCE: 16
cccggcggcg gtcacgaact ccttcaggac catgtg                        36

<210> SEQ ID NO 17
<211> LENGTH: 36
<212> TYPE: DNA
<213> ORGANISM: Artificial Sequence
<220> FEATURE:
<223> OTHER INFORMATION: PRIMER F223R top

<400> SEQUENCE: 17
cacatggtcc tgctggagcg cgtgaccgcc gccggg                        36

<210> SEQ ID NO 18
<211> LENGTH: 36
<212> TYPE: DNA
<213> ORGANISM: Artificial Sequence
<220> FEATURE:
<223> OTHER INFORMATION: PRIMER F223R bottom

<400> SEQUENCE: 18
cccggcggcg gtcacgcgct ccagcaggac catgtg                        36

<210> SEQ ID NO 19
<211> LENGTH: 36
<212> TYPE: DNA
<213> ORGANISM: Artificial Sequence
<220> FEATURE:
<223> OTHER INFORMATION: PRIMER L221K/F223R top

<400> SEQUENCE: 19
cacatcgtcc tgaaggagcg cgtgaccgcc gccggg                        36

<210> SEQ ID NO 20
<211> LENGTH: 36
<212> TYPE: DNA
<213> ORGANISM: Artificial Sequence
<220> FEATURE:
<223> OTHER INFORMATION: PRIMER L221K/F223R bottom

<400> SEQUENCE: 20
cccggcggcg gtcacgcgct ccttcaggac catgtg                        36

<210> SEQ ID NO 21
<211> LENGTH: 33
<212> TYPE: PRT
<213> ORGANISM: Artificial Sequence
<220> FEATURE:
<223> OTHER INFORMATION: ADDITIONAL 33 AMINO ACIDS TAG TO THE N-TERMINUS
      OF THE GFPs

<400> SEQUENCE: 21

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro
```

<210> SEQ ID NO 22
<211> LENGTH: 33
<212> TYPE: DNA
<213> ORGANISM: Artificial Sequence
<220> FEATURE:
<223> OTHER INFORMATION: PRIMER I125K

<400> SEQUENCE: 22
tacaaggtga agttcaaggg cgtgaacttc ccc                          33

<210> SEQ ID NO 23
<211> LENGTH: 33
<212> TYPE: DNA
<213> ORGANISM: Artificial Sequence
<220> FEATURE:
<223> OTHER INFORMATION: PRIMER L125K reverse

<400> SEQUENCE: 23
ggggaagttc acgcccttga acttcacctt gta                          33

<210> SEQ ID NO 24
<211> LENGTH: 33
<212> TYPE: DNA
<213> ORGANISM: Artificial Sequence
<220> FEATURE:
<223> OTHER INFORMATION: PRIMER I125R forward

<400> SEQUENCE: 24
tacaaggtga agttccgcgg cgtgaacttc ccc                          33

<210> SEQ ID NO 25
<211> LENGTH: 33
<212> TYPE: DNA
<213> ORGANISM: Artificial Sequence
<220> FEATURE:
<223> OTHER INFORMATION: PRIMER I125R reverse

<400> SEQUENCE: 25
ggggaagttc acgccgcgga acttcacctt gta                          33

<210> SEQ ID NO 26
<211> LENGTH: 18
<212> TYPE: PRT
<213> ORGANISM: Artificial Sequence
<220> FEATURE:
<223> OTHER INFORMATION: Synthetic peptide

<400> SEQUENCE: 26

Gly Ser Thr Ser Gly Ser Gly Lys Pro Gly Ser Gly Glu Gly Ser Thr
1               5                  10                  15

Lys Gly

<210> SEQ ID NO 27
<211> LENGTH: 86
<212> TYPE: DNA
<213> ORGANISM: Artificial Sequence
<220> FEATURE:
<223> OTHER INFORMATION: Primer for PCR

<400> SEQUENCE: 27
ccggatcccc tttggtgctg ccctctccgc tgccaggctt gccgctgccg ctggtgctgc    60
caaggaacag atggtggcgt ccctcg                                        86

<210> SEQ ID NO 28

-continued

```
<211> LENGTH: 86
<212> TYPE: DNA
<213> ORGANISM: Artificial Sequence
<220> FEATURE:
<223> OTHER INFORMATION: Primer for PCR

<400> SEQUENCE: 28
ccggatcccc cttggtgctg ccctccccgc tgccgggctt cccgctcccg ctggtgctgc      60
ccaggaacag gtggtggcgg ccctcg                                          86

<210> SEQ ID NO 29
<211> LENGTH: 24
<212> TYPE: DNA
<213> ORGANISM: Artificial Sequence
<220> FEATURE:
<223> OTHER INFORMATION: Primer for PCR

<400> SEQUENCE: 29
gtacgacgat gacgataagg atcc                                            24
```